United States Patent [19]
Suzuki et al.

[11] Patent Number: 5,879,288
[45] Date of Patent: Mar. 9, 1999

[54] ENDOSCOPE SYSTEM INCLUDING BOTH REUSABLE-TYPE AND COVER-TYPE ENDOSCOPES

[75] Inventors: Akira Suzuki; Hisao Yabe, both of Hachioji; Yoshihiro Iida, Tama; Hideo Itoh, Hachioji; Yoshio Tashiro, Hino; Minoru Yamazaki, Hachioji; Osamu Tamada, Hachioji; Keiichi Arai, Hachioji; Hiroshi Ishii, Hachioji; Masaaki Nakazawa, Hino; Koji Yamaya; Yasuhito Kura, both of Hachioji, all of Japan

[73] Assignee: Olympus Optical Co., Ltd., Tokyo, Japan

[21] Appl. No.: 600,650

[22] Filed: Feb. 13, 1996

Related U.S. Application Data

[63] Continuation of Ser. No. 154,794, Nov. 19, 1993, abandoned.

[30] Foreign Application Priority Data

Nov. 25, 1992 [JP] Japan .................................. 4-315232
Jan. 14, 1993 [JP] Japan .................................. 5-005354
Feb. 23, 1993 [JP] Japan .................................. 5-033509

[51] Int. Cl.$^6$ .......................................... A61B 1/00
[52] U.S. Cl. ........................ 600/176; 600/121; 600/132; 600/154; 600/156
[58] Field of Search .................................. 600/125, 127, 600/121, 123, 175–177, 178, 132; 348/72; 385/115, 117, 118

[56] References Cited

U.S. PATENT DOCUMENTS

| | | |
|---|---|---|
| 4,414,608 | 11/1983 | Furihata .................................. 600/132 |
| 4,576,144 | 3/1986 | Ishii .......................................... 600/132 |
| 4,601,284 | 7/1986 | Arakawa et al. .............................. 128/6 |
| 4,646,722 | 3/1987 | Silverstein et al. . |
| 4,715,360 | 12/1987 | Akui et al. .................................... 128/4 |
| 4,721,097 | 1/1988 | D'Amelio ..................................... 128/4 |
| 4,778,247 | 10/1988 | Carpenter .................................. 600/176 |
| 4,860,094 | 8/1989 | Hibino et al. ............................. 128/6 X |
| 4,862,258 | 8/1989 | Kidawara et al. ......................... 128/6 X |
| 4,865,018 | 9/1989 | Kanno et al. ................................ 128/6 |
| 4,878,485 | 11/1989 | Adair .......................................... 128/6 |
| 4,991,564 | 2/1991 | Takahashi et al. ........................... 128/4 |
| 5,051,824 | 9/1991 | Nishigaki .................................... 348/72 |
| 5,159,919 | 11/1992 | Chikama ...................................... 128/4 |
| 5,168,863 | 12/1992 | Kurtzek ....................................... 128/4 |
| 5,193,525 | 3/1993 | Silverstein et al. .......................... 128/4 |
| 5,201,908 | 4/1993 | Jones .......................................... 128/4 |
| 5,237,984 | 8/1993 | Williams, III et al. .................. 128/4 X |
| 5,257,617 | 11/1993 | Takahashi ................................. 600/123 |

*Primary Examiner*—John P. Leubecker
*Attorney, Agent, or Firm*—Armstrong, Westerman, Hattori, McLeland & Naughton

[57] ABSTRACT

An endoscope system provided with an electronic or optical endoscope is provided therein with an illuminating optical system, an observation optical system, a flow passage system and a forceps channel. Cleaning and disinfection operations are performed on the endoscope so that the endoscope is reusable. An electronic or optical cover type endoscope is provided therein with an illuminating optical system and an observation optical system. The cover type endoscope is used with an endoscope cover having a flow passage system and a forceps channel mounted on the cover type endoscope. The endoscope cover is discarded and replaced whereby the cover type endoscope is reused. Peripheral equipment for endoscope inspection used in combination with the endoscopes is capable of being selectively connected to any of the endoscopes.

5 Claims, 24 Drawing Sheets

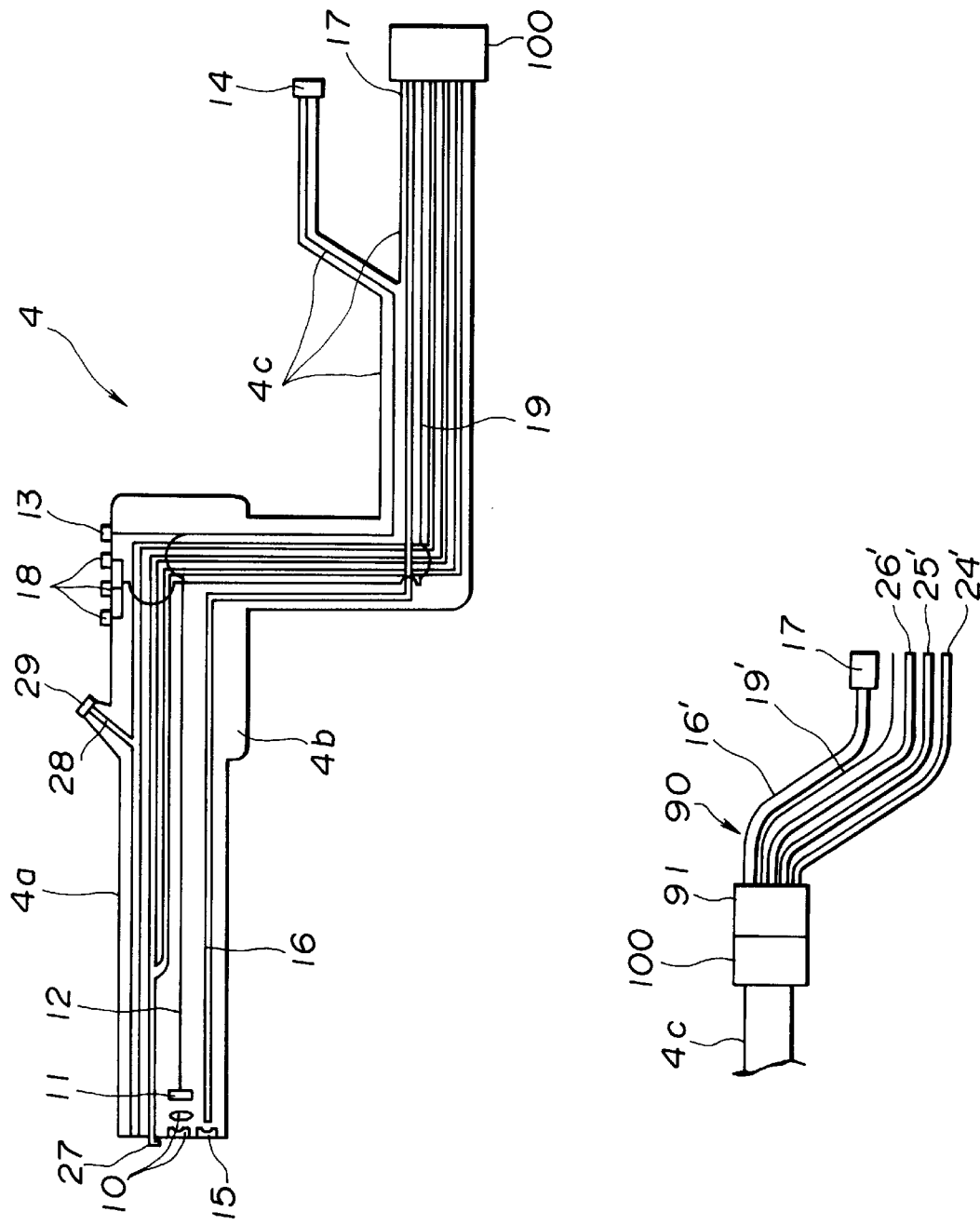

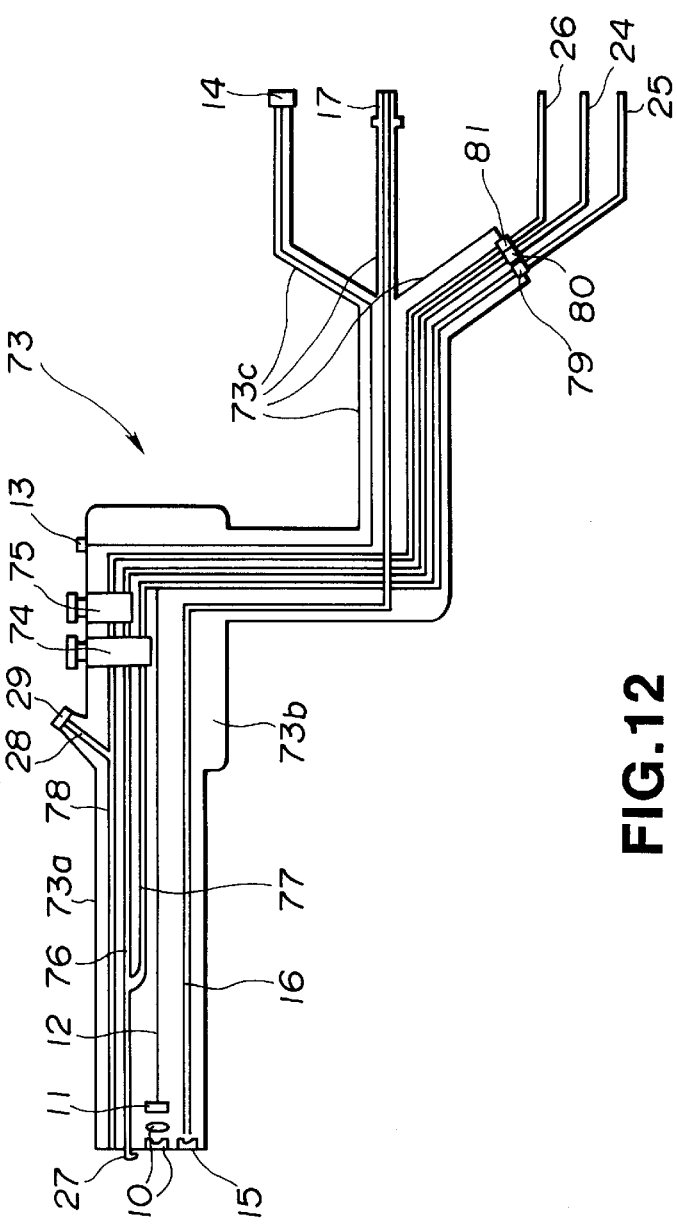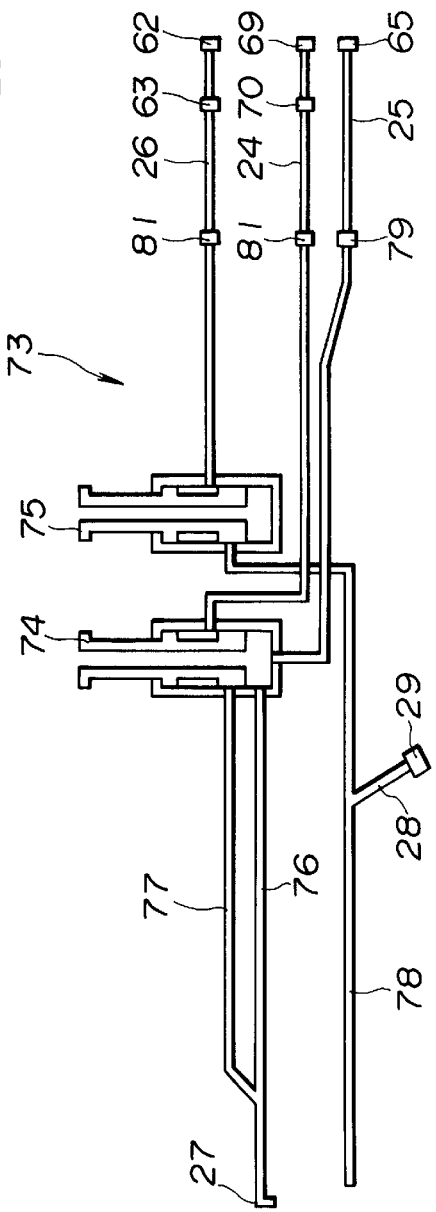

ANGLE OF FIELD

FIG.19(A)   FIG.19(B)
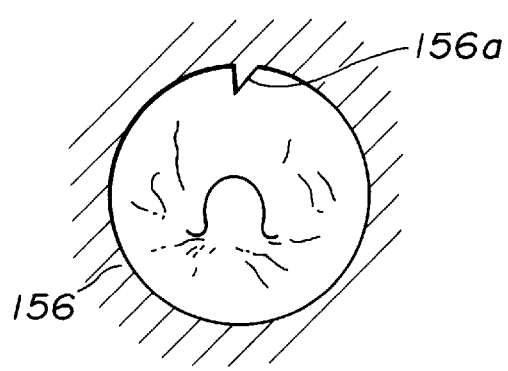
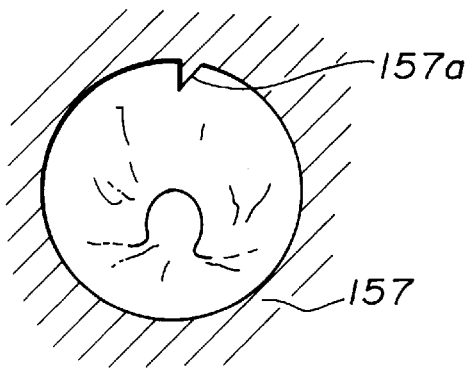
FIG.20
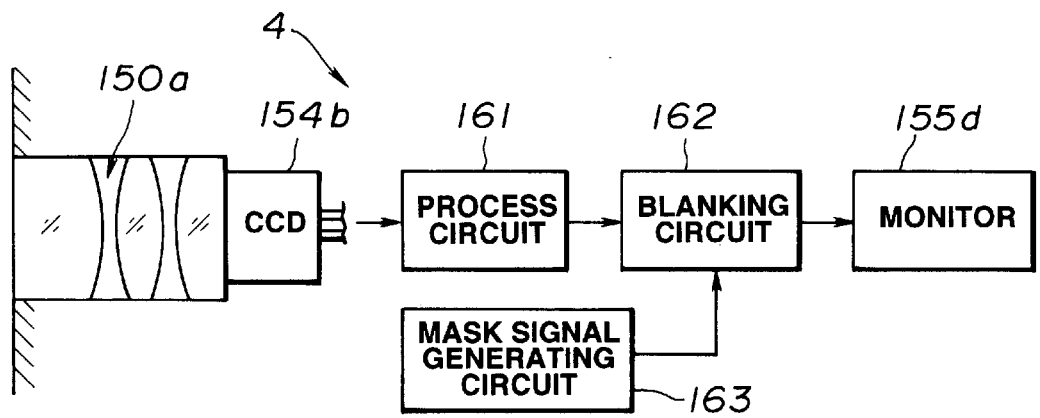
FIG.21
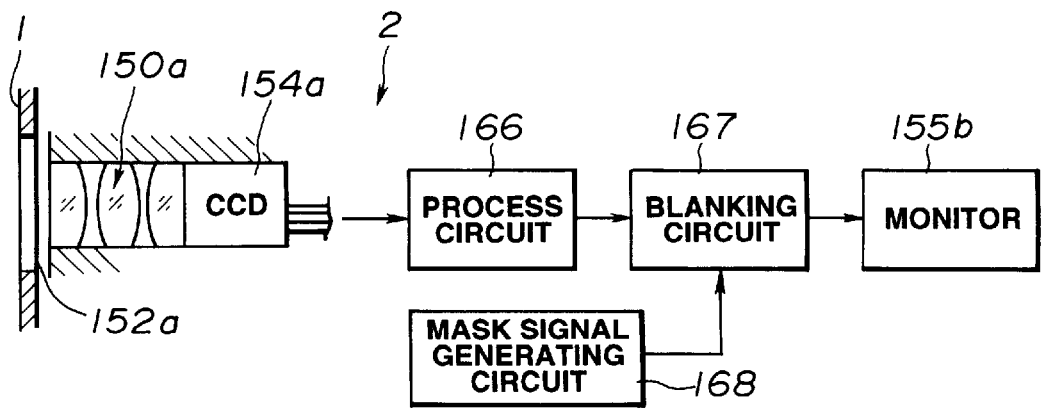

ENDOSCOPE SYSTEM INCLUDING BOTH REUSABLE-TYPE AND COVER-TYPE ENDOSCOPES

This application is a continuation of application Ser. No. 08/154,794 filed Nov. 19, 1993, now abandoned.

BACKGROUND OF THE INVENTION

1. Field of the Invention

The present invention relates to an endoscope system in which a cover type endoscope used with an endoscope cover being mounted and an endoscope used without an endoscope cover being mounted, are selectively connectable.

2. Description of the Related Art

In recent years, an endoscope has widely been used in both the medical art and industrial art fields. For example, an endoscope which is used in the medical art field has an inserting section which is inserted into a body cavity so as to be able to observe internal organs, or which uses a disposition or treatment instrument or tool inserted into a treating-instrument channel in the endoscope, so as to be able to perform various types of medical care or treatment. For this reason, in an endoscope system, various peripheral devices or units for endoscope inspection have been used in accordance with objects and uses of inspection.

In an endoscope system which includes peripheral units for endoscope inspection which are used for various objects and uses, it becomes much more an important or serious problem not only in that the endoscope system is useful for the insertion, but also in how it is possible to reduce the cost of inspection. Particularly, in the medical art field, reduction of medical cost is a great problem. Until now, various proposals have been introduced for reduction in inspection cost.

For example, restraint in unit or device purchase cost is one proposal for reduction of inspection cost.

A CCD which is arranged at a forward end of an inserting section of an electronic endoscope which projects a color endoscope image on a screen of a monitor unit has conventionally had two systems including a surface sequential type and a concurrent or simultaneous type. The CCD of the surface sequential type is adequate for observing fine lesion parts, because it is possible to produce an image having high resolution. The CCD of the simultaneous type is adequate for observation of internal organs which performs peristalsis, because the CCD of the simultaneous type can produce an image which has less blurring. For this reason, in a case where a user who has different endoscope systems uses the endoscopes properly in accordance with an inspection object, it has been required to prepare systems which include not only the endoscopes of two systems, but also video processors which are respectively adapted to the systems.

In view of the above, in order to solve the above-discussed problem, a video processor which copes with both the surface sequential type and the concurrent type is disclosed in U.S. Pat. No. 4,853,773. There is no necessity to purchase a system including separate video processors which cope or correspond respectively with or to the systems. Thus, the unit purchase cost of the user can be reduced, and a space of an inspection room can effectively be utilized, because it is sufficient with a single video processor and a single accompanying or attendant system.

Further, as another proposal for reduction in the inspection cost, there is one in which the number of uses of the endoscope per one day increases so that an inspecting cost is reduced.

Generally, in a case where an endoscope which has been used once for inspection and treatment within a body cavity is again used for the other patients, disinfection chemicals, or an ethylene oxide gas must be used to perform washing or cleaning and disinfection of the endoscope after completion of the inspection and the treatment, in order to prevent infection from occurring between the patients through the endoscope. However, since about one hour is required to sufficiently disinfect the endoscope, which is provided with very small lines, the cleaning and disinfection time becomes a dead time. When it is assumed that the inspecting time per use is about five (5) hours, only four (4) persons can be inspected per a single day by a single endoscope, if it is assumed that the endoscope inspecting time per one every fifteen (15) minutes.

In order to solve the above-discussed problem, if a plurality of endoscopes are prepared, and if the endoscopes which have been cleaned and disinfected are used during the cleaning and disinfection time, inspection of twenty (20) persons per five (5) hours is made possible by subsequent use of five (5) endoscopes when the inspecting time is fifteen (15) minutes and the cleaning time is one (1) hour. In this case, however, there occurs a problem that the purchase of five (5) endoscopes is required.

In view of the above, U.S. Pat. No. 4,646,722 has proposed a throwaway or disposable endoscope sheath (hereinafter referred to as "endoscope cover"). The endoscope cover is arranged such that the endoscope cover covers an endoscope inserting section before inspection, an endoscope covered by the endoscope cover is inserted into a body cavity, the endoscope cover which has covered the endoscope inserting section is discarded after completion of the inspection and treatment, and a new endoscope cover is used to cover the endoscope and is left in place for subsequent inspection. By the use of the endoscope cover, it is possible to bring the cleaning and disinfection time (one hour) to a cover replacement or exchange time of only ten (10) minutes. Specifically, since twenty-five (25) minutes, which is the sum of the endoscope inspecting time of fifteen (15) minutes and the cover replacement time of ten (10) minutes, forms a single cycle, it is possible to perform inspection of twelve (12) persons per five (5) hours by only a single endoscope. Thus, it is possible to considerably reduce the endoscope inspecting cost per use.

However, in a case where the above-described disposable endoscope cover is applied to all of the endoscope inspections, the cost of the endoscope cover is generated every inspection, and it is not preferable in view of environmental maintenance or preservation to treat the endoscope cover as industrial waste or refuse. Thus, it has been desired to reduce the industrial waste even in a minor way.

In view of the above, we proposed that, in order to make an attempt to reduce the inspection cost, two types of endoscopes including an endoscope which is reused while being cleaned and disinfected without the endoscope cover being mounted (hereinafter referred to as "reusable type endoscope") and an endoscope which is used with an endoscope cover being mounted thereon (hereinafter referred to as "cover type endoscope") are suitably combined with each other so as to be used in inspection.

Specifically, the cover type endoscope is used twice in a dead time in which the reusable type endoscope is cleaned and disinfected, whereby a field of practical use of the reusable type endoscope which is low in running cost can be formed. Further, the endoscopes of two types are suitably combined with each other, whereby thirteen (13) persons can be inspected for about five (5) hours, and the number of uses of the endoscope cover can be reduced to ⅔. Thus, it is possible to cope with inspection cost and an environmental problem.

However, in an endoscope system for performing endoscope inspection, peripheral tools or equipment and materials for endoscope inspection such as a light source unit, a video processor, a fluid control unit, treatment equipments, forceps plugs, mouth pieces, or inserting auxiliary equipment are required in addition to an endoscope.

For this reason, in the reusable type endoscope system, it is assumed that cleaning and disinfection of the endoscope are carried out in every case. Thus, various devices or contrivances are carried out in order to improve detachable workability or operability between the endoscope and the peripheral equipment for the endoscope. Accordingly, the structure is complicated and is large-sized. Elements or members which can be born against repeated use are used in a treating-equipment inserting channel into which a treatment equipment is inserted, and a forceps-plug detachable or mounting and demounting portion.

Meanwhile, in the cover type endoscope system, since the number of mounting and demounting cycles between an endoscope body and peripheral equipment for endoscope inspection decreases drastically, simplification, small-sizing and reduction in cost are desired more than improvement in the mounting and demounting operability. Accordingly, it becomes a preference or priority problem to reduce the cost and to reduce, in outer diameter, the inserting section more than durability to alleviate a burden of a patient.

In this manner, in the conventional endoscope system, the structure of the peripheral equipment for endoscope inspection, which are used in the reusable type endoscope system, and the structure of the peripheral equipment for endoscope inspection, which are used in the cover type endoscope system, are arranged respectively under the original or unique backgrounds. Accordingly, in order to use both types of endoscopes together, in single-day inspection, it has been required to correspondingly replace or exchange also the peripheral equipment for endoscope inspection together with the endoscope. Thus, in a case where a replacement time of these equipments is also taken into consideration, an operational method in which the cover type endoscope is used in the dead time in which the reusable type endoscope is cleaned and disinfected, has been very difficult in actuality.

SUMMARY OF THE INVENTION

It is an object of the invention to provide an endoscope system which is capable of suitably selecting either one of a reusable type endoscope and a cover type endoscope to use the same, depending upon a using object and which is capable of realizing endoscope medical treatment in a most effective manner.

It is another object of the invention to provide an endoscope system which is capable of observing without causing a feeling of physical disorder, similarly to a reusable type endoscope, without the fact that the field of view is narrowed by an endoscope cover under such a condition that the endoscope cover is mounted, and which is provided with a cover type endoscope which is superior in operability without injuring or spoiling the insertability of treatment equipment.

It is a further object of the invention to provide an endoscope system which is capable of easily connecting an outside connecting portion of a cover type endoscope to a piece of peripheral equipment for inspection for a reusable type endoscope, and which is superior in handling-ability, which is economical and which is developable.

Briefly, according to the invention, there is provided an endoscope system comprising:

an electronic or optical reusable type endoscope provided therein with an illuminating optical system, an observation optical system, a flow passage system and a forceps channel, cleaning and disinfection being applied to the reusable type endoscope so that the reusable type endoscope is reused;

an electronic or optical cover type endoscope provided therein with an illuminating optical system and an observation optical system, the covering endoscope being used with an endoscope cover having a flow passage system and a forceps channel being mounted on the covering endoscope, the endoscope cover being discarded and replaced whereby the covering endoscope is reused; and peripheral equipment for endoscope inspection used in the combination of endoscopes, the peripheral equipment being selectively connectable to any of the endoscopes.

These objects and advantages of the present invention will become further apparent from the following detailed explanation.

BRIEF DESCRIPTION OF THE DRAWINGS

FIGS. 1 to 10 relate to a first embodiment of the present invention;

FIG. 1 is an explanatory view showing a combination arrangement of an endoscope system;

FIG. 2 is an explanatory view showing a schematic arrangement of a covering electronic endoscope;

FIG. 3 is an explanatory view showing a schematic arrangement of a covering fiber scope;

FIG. 4 is an explanatory view showing a schematic arrangement of an endoscope cover;

FIG. 5 is an explanatory view showing a schematic arrangement of a reusable type electronic endoscope;

FIG. 6 is an explanatory view showing a schematic arrangement of a reusable type fiber scope;

FIG. 7 is an explanatory view showing a schematic arrangement of a fluid unit;

FIG. 8 is an explanatory view showing a schematic arrangement of a video processor;

FIG. 9 is an explanatory view showing a schematic arrangement of a light source unit;

FIG. 10 is an explanatory view showing a connector portion of the reusable type electronic endoscope illustrated in FIG. 5 and a connector receptor which is connected to the connector portion;

FIGS. 11 and 12 relate to an endoscope which is used in the endoscope system according to the invention;

FIG. 11 is an explanatory view showing a schematic arrangement of an electronic endoscope which controls a fluid passage system by a mechanical switch;

FIG. 12 is an explanatory view showing a schematic arrangement of the fluid passage system of the electronic endoscope illustrated in FIG. 11;

FIG. 13 is a cross-sectional view describing a schematic arrangement of a curvature portion of a cover type endoscope under a curvature condition;

FIG. 14 is a cross-sectional view describing a schematic arrangement of a port portion of the cover type endoscope;

FIGS. 16 to 18 relate to an optical system of the cover type endoscope which is used in the endoscope system according to the invention;

FIG. 16 is a cross-sectional view showing an arrangement of a forward end of the cover type endoscope;

FIGS. 19(A) and 19(B) are explanatory views showing an observing mask of a fiber scope;

FIG. 20 is a block diagram showing signal processing in the reusable type endoscope of a concurrent or simultaneous image-pickup system;

FIG. 21 is a block diagram showing signal processing in the cover type endoscope of a concurrent image-pickup system;

FIG. 29 is a view showing a schematic arrangement of a cover type endoscope system;

FIG. 30 is a side elevational view of a connector which is provided on a universal cord on the side of the covering endoscope;

FIG. 31 is a perspective view of an adaptor;

FIG. 37 is a perspective view showing the adaptor;

FIG. 38 is a longitudinal cross-sectional view of FIG. 37;

FIG. 39 is a wiring diagram of a principal portion of the cover-type endoscope system;

FIG. 40 is a side elevational view partly including a cross section showing a fiber scope on which an endoscope is mounted;

FIG. 41 is a side elevational view showing a part or portion of an operating section of a video scope;

DETAILED DESCRIPTION OF THE PREFERRED EMBODIMENTS

An embodiment of an endoscope system according to the present invention will be described with reference to FIGS. 1 to 12.

Figure 1:
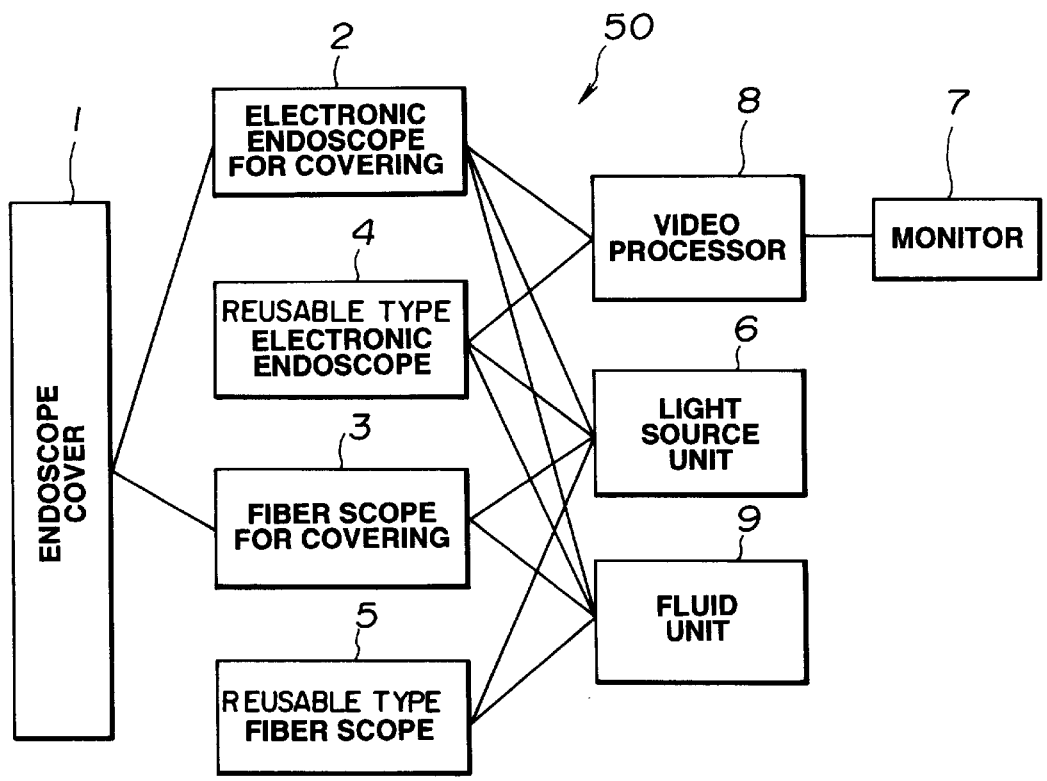

As shown in FIG. 1, an endoscope system 50 according to the present invention comprises a covering electronic endoscope 2 and a covering fiber scope 3, which are used with an endoscope cover 1 being mounted, a reusable type electronic endoscope 4 and a reusable type fiber scope 5 which are used without the endoscope cover 1 being mounted and which subsequently are cleaned and disinfected, a light source unit 6 for supplying an illuminating light to illuminating optical systems which are provided respectively in the endoscopes, a video processor 8 for converting an image of an observed part illuminated by the illuminating light, to an electric signal for displaying the image on a monitor 7, and various pieces of peripheral equipments for endoscope inspection, such as a fluid control unit 9 for performing gas feeding, water feeding, and suction to a passage system which is arranged in an endoscope to be described subsequently.

In the present embodiment, illuminating optical means, observation optical means and a passage system are provided within the reusable type electronic endoscope 4 and the fiber scope 5. Illuminating optical means and observation optical means are provided within the cover type electronic endoscope 2 and the fiber scope 3 without the provision of the flow passage system. The endoscope cover 1 formed therein with a passage system is mounted on the cover type electronic endoscope 2 and the fiber scope 3.

In connection with the above, the reusable type electronic endoscope 4 and the fiber scope 5, and the cover type electronic endoscope 2 and the fiber scope 3 are connectable to the light source unit 6 and the fluid control unit 9. Either one of the covering electronic endoscope 2 and the reusable type electronic endoscope 4 are connectable to the video processor 8.

Figure 2:
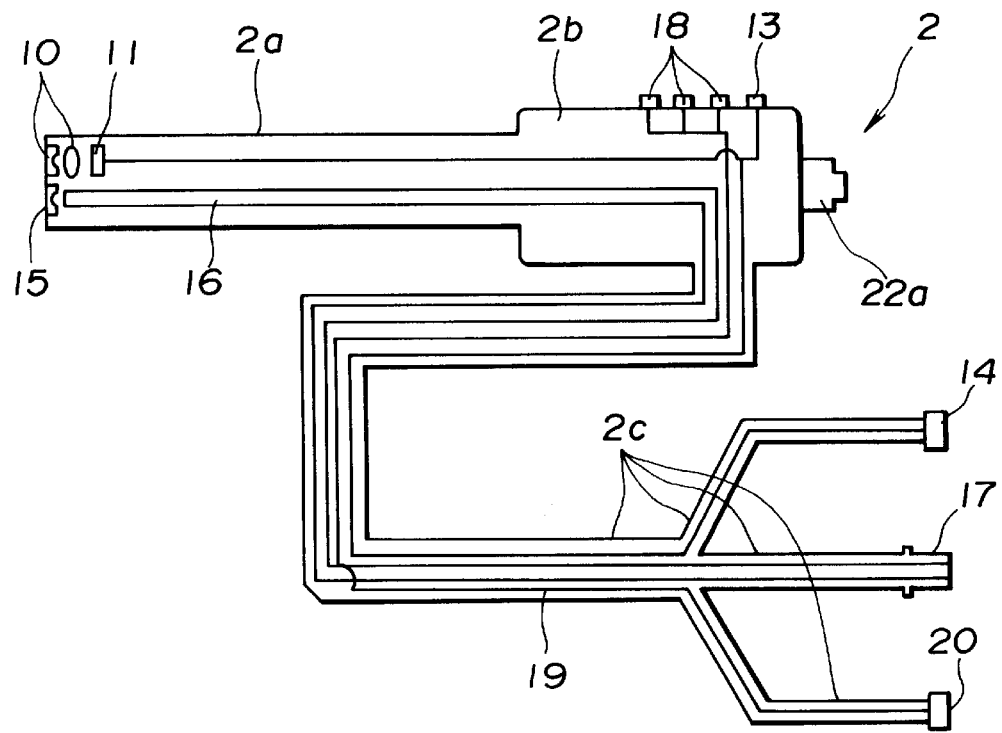

As shown in FIG. 2, the covering electronic endoscope 2 is arranged such that an observation optical system 10, a solid-state image pickup element 11 and an illuminating lens 15 are arranged at a forward end of a bendable inserting section 2*a*. The inserting section 2*a* of the endoscope has a cross section thereof which is formed substantially into a semicircle. The inserting section 2*a* has a rearward end thereof which is provided with an operating section 2*b* which is formed with a convex projection 22*a* the same in shape or configuration as an ocular portion of a fiber scope to be described subsequently. A freeze switch 13 is provided on the operating section 2*b* for freezing the image displayed on the monitor 7. Switches 18 are for controlling the fluid control unit 9 to perform gas feeding, water feeding and suction.

Moreover, inserted into a universal cord 2*c* which extends from a side surface of the operating section 2*b* are a signal cable 12 which extends from the solid-state image-pickup element 11, a light guide fiber 16 terminating against the illuminating lens 15, and a signal line 19 which extends from the gas feeding, water feeding and suction switches 18. The universal cord 2*c* branches into a signal cable connector 14, a light guide connector 17 and a signal-line connector 20.

Figure 3:
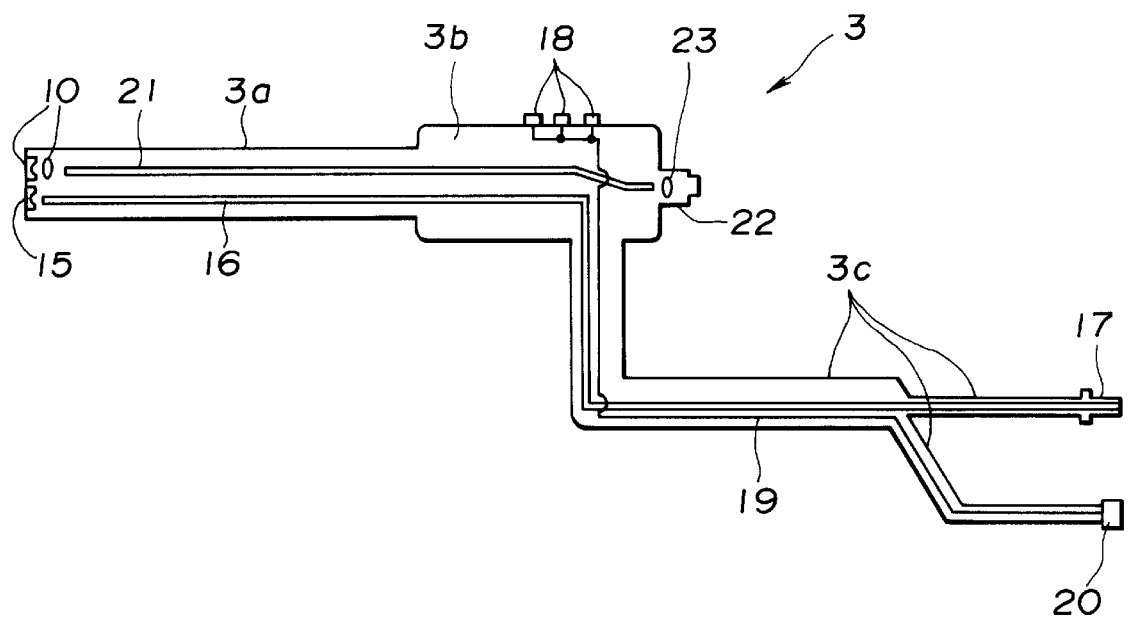

Similarly, the covering fiber scope 3 illustrated in FIG. 3 is arranged such that the observation optical system 10 and the illuminating lens 15 are arranged at a forward end of a bendable inserting section 3*a*, and the endoscope inserting section 3*a* has a cross section thereof which is formed substantially into a semicircular configuration. Inserted through the inserting section 3*a* is an image guide fiber 21 for transmitting an observation image imaged by the observation optical system 10 so that an observation part can be observed by an ocular section 22 which is provided on an operating section 3*b*. Furthermore, the gas feeding, water feeding and suction switches 18 which are provided on the operating section 3*b* are operated whereby the fluid control unit 9 is controlled so that gas feeding, water feeding and suction can be performed.

Further, inserted through a universal cord 3*c* which extends from the side surface of the operating section 3*b* are a light guide fiber 16 which terminates against the illuminating lens 15, and a signal line 19 which extends from the gas feeding, water feeding and suction switches 18. A light guide connector 17 and a signal-line connector 20 branch.

Figure 4:
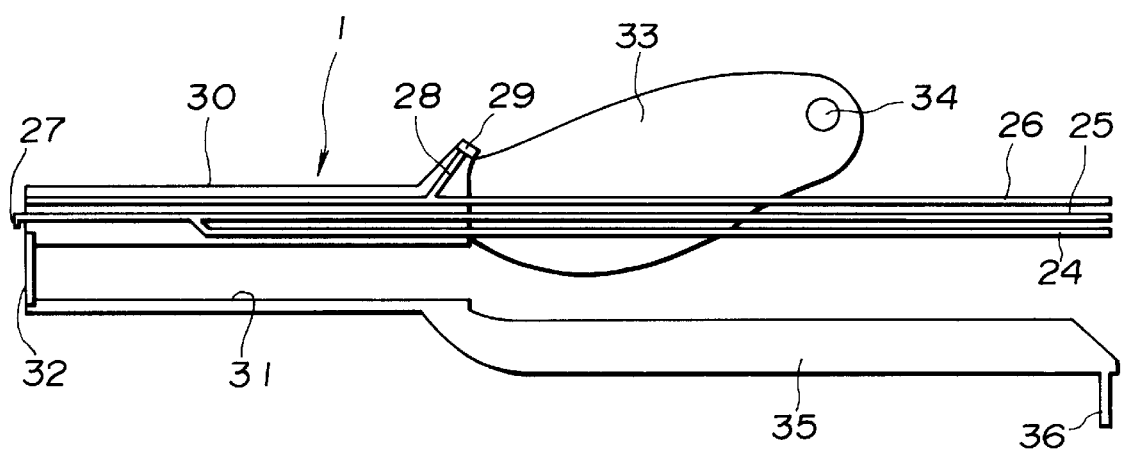

As shown in FIG. 4, the endoscope cover 1 is made of an elastic or flexible body such as rubber, and comprises an inserting section cover 30 having a scope inserting section 31 having a cross section thereof of substantially a semicircle into which the covering electronic endoscope and the covering fiber scope 3 (hereinafter referred generally to as "covering endoscope"), an inserting-section cover 33 connected to be liquid tight to the inserting-section cover 30 and formed of vinyl so as to cover the operating section 2*b* and the operating section 3*b* of the covering endoscope, and a universal cord cover 35 formed of elongated strip-like vinyl which covers the universal cord 2*c* and the universal cord 3*c* of the covering endoscope.

A water feeding tube 24, a gas feeding tube 25 and a suction tube 26 which are formed of a resinous element such a silicon or teflon are arranged in the inserting-section cover 30. A forceps tube 28 is formed in communication with the suction tube 26. A forceps plug 29 is provided on a portion of the forceps tube 28.

Moreover, a lens cover 32 is arranged to be liquid tight at a forward end of the scope inserting section 31 which is provided in the inserting-section cover 30, while a gas feeding and water feeding nozzle 27 is provided at a forward end of a tube formed into a single tube from the water feeding tube 24 and the gas feeding tube 25 in opposed relation to the lens cover 32.

In connection with the above, the operating-section cover 33 is formed with a projection 22*a* which is provided on a rearward end of the operating section 2*b* of the covering electronic endoscope, and a through bore 34 slightly smaller in diameter than the ocular portion 22 of the covering fiber scope 3. Moreover, a detachable velcro band fastener 36 formed of resin adhesive tape is provided on an end of the universal cord cover 35. Furthermore, when the projection 22*a* is not formed on the covering electronic endoscope 2, the through bore 34 provided in the endoscope cover 1 is mounted so as to be closed by a cap (not shown). Further, an end of the water feeding tube 24, an end of the gas feeding tube 25 and an end of the suction tube 26, which extend from the endoscope cover 1, are put together whereby it is possible to easily perform winding of the universal cord cover 35.

Figure 5:
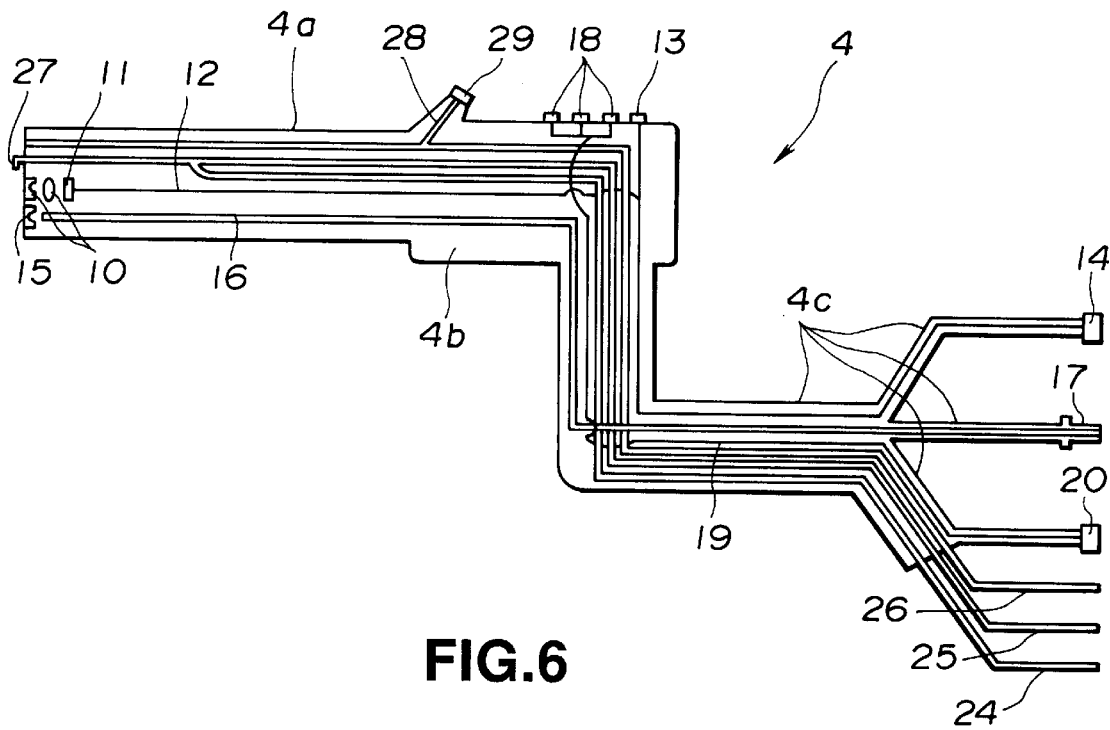

As shown in FIG. 5, the reusable type electronic endoscope 4 is arranged such that the observation optical system 10, the solid-state image-pickup element 11 and the illuminating lens 15 are arranged on a forward end of the bendable inserting section 6*a*, and the water feeding tube 24, the gas feeding tube 25 and the suction tube 26 similar to those of the endoscope cover 1 are arranged on the inserting section 6*a*. The forceps tube 28 is in communication with the suction tube 26. The forceps plug 29 is arranged on the side of the forceps tube 28. The gas feeding and water feeding nozzle 27 is provided at a forward end of the tube at which the water feeding tube 24 and the gas feeding tube 25 are brought to form a single tube such that the forward end of the nozzle 27 is opposed against the observation optical system 10. Moreover, an inserting section 4*a* has a rearward end thereof at which an operating section 4*b* is provided. Arranged on the operating section 6*b* are the switch 13 for switching an image displayed on the monitor image plane and the gas feeding, water feeding and suction switches 18 for controlling the fluid control unit 9 to perform gas feeding, water feeding and suction.

Inserted into a universal cord 4*c* which extends from a side surface of the operating section 4*b* are the signal cable 12 which extends from the solid-state image-pickup element 11, the light guide fiber 16 confronted against the illuminating lens 15, the signal line 19 which extends from the gas feeding, water feeding and suction switches 18, the water feeding tube 24, the gas feeding tube 25, and the suction tube 26. The universal cord 6*c* branches into the signal cable connector 14, the light guide connector 17 and the signal-line connector 20. The water feeding tube 24, the gas feeding tube 25 and the suction tube 26 extend from the universal cord 6*c*.

Figure 6:
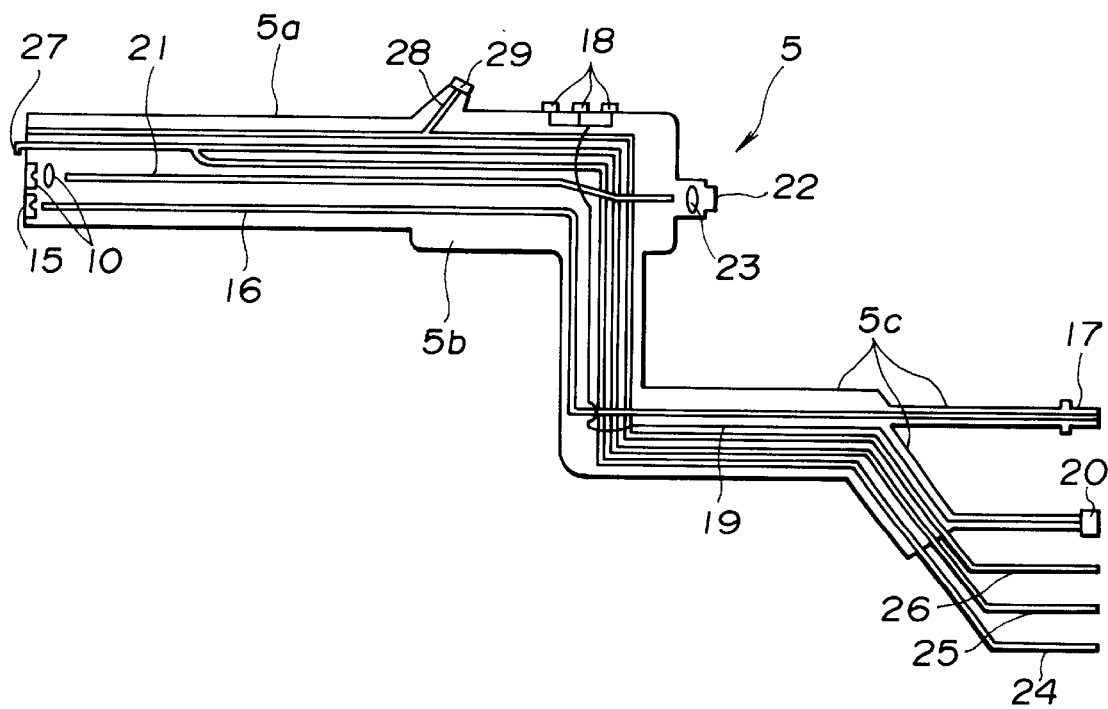

Similarly, the reusable type fiber scope 5 illustrated in FIG. 6 is arranged such that the observation optical system 10 and the illuminating lens 15 are arranged at a forward end of a bendable inserting section 5*a*, and the reusable type fiber scope 5 is inserted through the water feeding tube 24, the gas feeding tube 25 and the suction tube 26. The forceps tube 28 is in communication with the suction tube 26. The forceps plug 29 is provided at the side of the forceps tube 28.

Moreover, the gas feeding and water feeding nozzle 27 is provided at the forward end of the tube in which the water feeding tube 24 and the gas feeding tube 25 form a single tube, in such a manner that the forward end of the nozzle 27 is opposed against the observation optical system 10 and the illuminating lens cover 15. Furthermore, the image guide fiber 16 for transmitting an observing image which is imaged by the observation optical system 10 is inserted into the inserting section 5a. The inserting section 5a has a rearward end thereof at which an operating section 5a provided with the ocular portion 22 of the fiber scope is provided. The gas feeding, water feeding and suction switches 18 provided at the operating section 3b are operated whereby the fluid control unit 9 is controlled.

Inserted through a universal cord 5c which extends from the side surface of the operating section 3b are the light guide fiber 16 which terminates against the illuminating lens 15, and the signal line 19 which extends from the gas feeding, water feeding and suction switches 18, the water feeding tube 24, the gas feeding tube 25, and the suction tube 26. The universal cord 5c branches into the light guide connector 17 and the signal-line connector 20. The water feeding tube 24, the gas feeding tube 25 and the suction tube 26 extend from the universal cord 5c.

Here, a method of mounting the endoscope cover on the covering endoscope will briefly be described.

First, the endoscope cover 1 packed in a sterilization pack is taken out. Then, the inserting section 2a of the covering electronic endoscope 2 is inserted into the scope inserting bore 31 which is provided in the inserting-section cover 30 of the endoscope cover 1. The forward end surface of the inserting section 2a is abutted against the lens cover 32 which is arranged at the forward end of the scope inserting bore 31. Thus, the mounting operation on the inserting section 2a is completed or ended.

Subsequently, the water feeding tube 24, the gas feeding tube 25 and the suction tube 26, which extend from the inserting-section cover 30 of the endoscope cover 1, are made parallel to the operating section 2b, while the through bore 34 in the operating-section cover 33 and the projection 22' provided on the operating section 2b are positioned so that the operating section 2b is wrapped by the operating-section cover 33. Further, the water feeding tube 24, the gas feeding tube 25 and the suction tube 26 are made parallel to the universal cord 2c. Thus, the universal-cord cover 35 is wound around the universal cord 2c. Thus, mounting of the endoscope cover 1 on the covering electronic endoscope 2 is completed.

Figure 7:
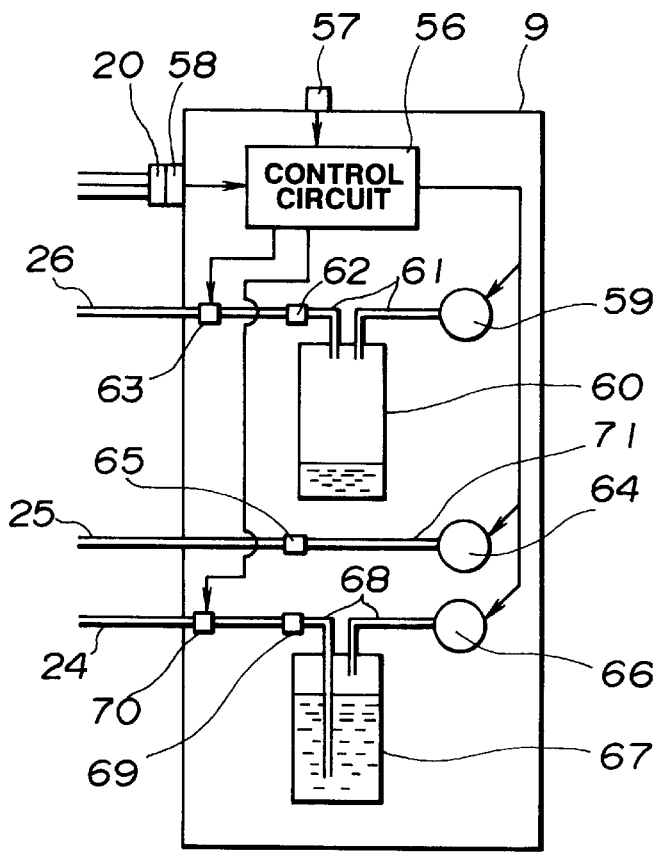

As shown in FIG. 7, connected to the fluid control unit 9 are the water feeding tube 24, the gas feeding tube 25 and the suction tube 26 which extend from the endoscope cover 1 and the reusable type endoscopes 4 and 5.

The water feeding tube 24 is in communication with a first connecting base 69 through a first pinch valve 70, and is connected to a water feeding tank 67 and a water feeding pump 66 by a first connecting pipe 68. The gas feeding tube 25 is in communication with a second connecting pipe 71 through a second connecting base 65, and is connected to a gas feeding pump 64. The suction tube 26 is in communication with a third connecting base 62 through a second pinch valve 63, similarly to the water feeding tube 24, and is connected to the suction tank 67 and the suction pump 66 by a third connecting pipe 61.

Moreover, the fluid control unit 9 is provided with an electric connector receptacle 58 to which the electric connector 20 of the reusable type endoscope and the covering endoscope is connected. The electric connector receptacle 58 and the electric connector 20 are connected to each other, whereby a control signal is inputted to a control circuit 56 by operation of the gas feeding, water feeding and suction switches 19 which are provided on the operating sections 2c, 3c, 4c and 5c, so that the first pinch valve 70 and the second pinch valve 63, and the water feeding pump 66, the gas feeding pump 64 and a suction pump 59 are controlled in ON and OFF.

In connection with the above, a change-over switch 57 which is provided on the fluid control unit 9 is a switch for changing over a control system of the fluid control unit 9 to an electric switch control system or a mechanical switch control system to be described subsequently. In a case where the electric switch control system is selected, the gas feeding pump 64 is driven during the fact that the gas feeding switches 18 are depressed. During the fact that the water feeding switches 18 are depressed, the water feeding pump 66 is driven, and the first pinch valve 70 opens so that water feeding can be performed. Furthermore, when the suction switches 18 are depressed, the suction pump 59 is driven so that the second pinch valve 63 opens so as to be capable of performing suction.

Figure 8:
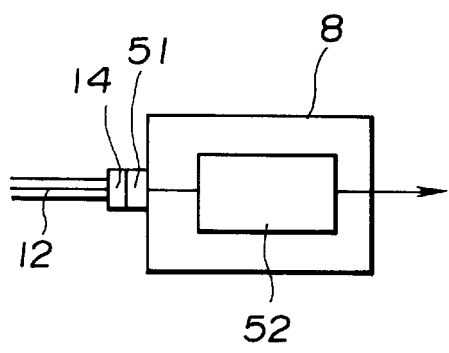

Further, as shown in FIG. 8, the arrangement is such that the electric connector 14 which extends from the universal cords 2c and 4c is connected to a electric connector receptacle 51 which is provided on the video processor 8. The electric connector 14 is connected to the electric connector receptacle 51, whereby a signal from the solid-state image-pickup element 11 and a signal from the switch 13 are inputted to a video processing circuit 52 through the signal line 12. The electric signal which is converted by the solid-state image pickup element 11 is converted to a standard video signal such as NTSC by the video processor 8 so that an observation image is displayed on the monitor 7, and the image is controlled by an image switching signal which is inputted from the switch 13.

Figure 9:
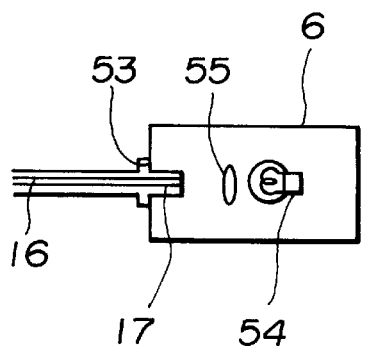

Moreover, as shown in FIG. 9, the light guide connector 17 which extends from the universal cords 2c, 3c, 4c and 5c is connected to a light guide connector receptacle 53 which is provided on the light source unit 6, whereby the illuminating light from an illuminating lamp 54 is condensed to an end surface of the light guide connector 17 by a condenser lens 55 and is transmitted into the body cavity through the light guide.

In connection with the above, in the above-description, connection to the fluid control unit 9, the video processor 8, the light source unit 6 in the cover type endoscope system in which the endoscope cover 1 is mounted on the covering electronic endoscope 2 has been described. However, in the electronic endoscope 4 shown in FIG. 5, connection can be made similarly to the covering electronic endoscope 2 except that the endoscope cover 1 is not mounted. Furthermore, connection of the electric connector 20 to the video processor 8 is not necessary for the covering fiber scope 3 shown in FIG. 3. Accordingly, except for this, connection can be made similarly to the covering electronic endoscope 2. Further, in the fiber scope 5 shown in FIG. 6, connection can be made similarly to the covering electronic endoscope 2 except that mounting of the endoscope cover 1 and connection of the electric connector 20 to the video processor 8 are unnecessary.

In this manner, the endoscope system according to the invention can suitably select and use the electronic endoscope that is the reusable type endoscope and the fiber scope, and the covering electronic endoscope that is the cover type endoscope and the covering fiber scope in accordance with a required used of the scope, such as the presence and absence of infection cases of patients, parts to be inspected and the like. For example, if the cover type endoscope is used for a patient who is known to be infections with a disease such as hepatitis, and if only the endoscope cover is discarded after inspection, the time required for disinfection sterilization for reusing the reusable type endoscope can be considerably reduced, and it is possible to prevent infection from being generated.

Moreover, if the reusable type endoscope is used for an endoscope inspection of a patient who does not fear an infections condition, it is possible to sufficiently replace the endoscope cover of the cover type endoscope because of the fact that the endoscope inspection is performed by the reusable type endoscope. Accordingly, it is possible to efficiently or effectively perform the endoscopic inspection.

By the way, as shown in FIG. 10, in the electronic endoscope 4 which is provided with a connector 100 in which the water feeding tube 24, the gas feeding tube 25, the suction tube 26, the light guide fiber 16 and the signal line 19 are put together in a unit, a connector receptacle 91 which is connected to the connector 100 is provided, and a code 90 within which a signal line 19', a water feeding tube 24', a gas feeding tube 25', a suction tube 26' and a light guide fiber 16' provided at a forward end thereof, with the light guide connector 17 extending from the connector receptacle 91. Specifically, the signal line 19', the water feeding tube 24', the gas feeding tube 25', the suction tube 26' and the light guide connector 17, which extend from the connector receptacle 91, are first connected to the fluid control unit 9 and the light source unit 6. Then, the connector 100 and the connector receptacle 91 are connected to each other. Thus, it impossible to quickly perform connection to the fluid control unit 9 and the light source unit 6. The other arrangements are similar to the electronic endoscope illustrated in FIG. 5. The same or identical reference numerals are applied to the same or identical elements, and the description thereof will be omitted.

FIGS. 11 and 12 show a scope which is used in the endoscope system according to the present invention. FIG. 11 is an explanatory view showing a schematic arrangement of an electronic endoscope in which a passage system is controlled by a mechanical switch, while FIG. 12 is an explanatory view showing a schematic arrangement of the passage system of the electronic endoscope illustrated in FIG. 11.

An electronic endoscope 73 illustrated in FIG. 11 performs control by mechanical switches 74 and 75, in addition to the fact that the passage system is controlled by the gas feeding, water feeding and suction switches 18.

Moreover, as shown in FIG. 12, the gas feeding tube 25 which is connected to a fourth connecting base 79 is in communication with a bottom surface of the gas feeding and water feeding button 74 of the electronic endoscope 73. The water feeding tube 24 which is connected to a fifth connecting base 80 is in communication with a portion adjacent to a proximal end of a side surface of the gas feeding and water feeding button 74. Furthermore, a water feeding pipe 77 extends toward the forward end of the inserting section from a location above a side surface of the gas feeding and water feeding button 74 adjacent to a forward end thereof, while a gas feeding tube 76 extends toward the forward end of the inserting section from a location below the side surface of the gas feeding and water feeding button 74 adjacent to the forward end thereof. The gas feeding and water feeding button 74 is moved whereby the gas feeding tube 76 and. the gas feeding tube 25 are in mechanical communication with each other, or the water feeding tube 77 and the water feeding tube 24 are in communication with each other.

Meanwhile, the suction tube 26 which is connected to a sixth connecting base 81 is in communication with a side surface of the suction button 75 adjacent to a proximal end thereof. A suction tube 78 extends from the side surface adjacent to the forward end toward the forward end of the inserting section. The suction button 75 is moved whereby the suction pipe 78 and the suction tube 26 are mechanically in communication with each other. In this connection, the water feeding tube 24, the gas feeding tube 25 and the suction tube 26 are connected to the fluid control unit 9. The rest of this arrangement is similar to the electronic endoscope illustrated in FIG. 5. Thus, the same or identical reference numerals are applied to the same or identical elements, and the description thereof will be omitted.

In connection with the above, it is needless to say that the fiber scope which mechanically controls the passage system is similarly arranged.

The endoscope cover which is used in the endoscope system according to the invention will be described with reference to FIGS. 13 and 14.

Figure 13:
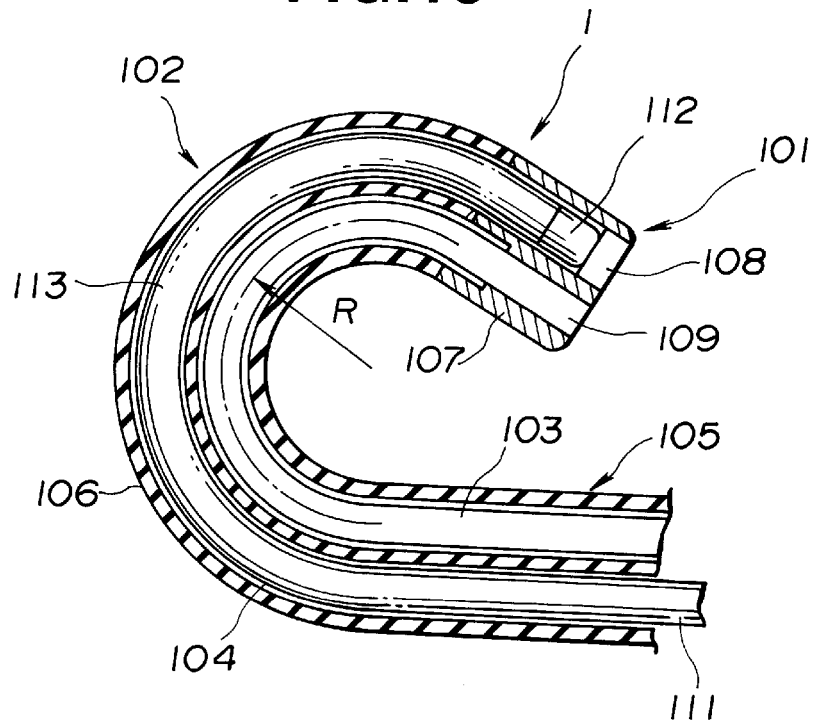
FIGS. 13 and 14 relate to an endoscope cover which is used in the endoscope system.

As shown in FIG. 13, an inserting-section cover portion 105 of the endoscope cover 1 comprises a cover tube 106 and a hard forward-end rigid portion 107. A lens cover 108 is arranged on the forward-end rigid portion 107, and an opening 109 in communication with the forceps channel is formed in the forward-end rigid portion 107.

An inserting section 111 of the endoscope has a curvature portion 113. A forward end 112 of the inserting section 111 is abutted against an inward surface of the lens cover 108. The curvature portion 113 is curved upwardly and rightwardly when the curvature portion 113 is bent to the maximum curvature angle. A curvature portion 102 of the cover tube 106 of an inserting-section cover portion 101 is curved in accordance with a curvature motion of the inserting section 111 of the endoscope which is inserted into the curvature portion 102. In the present embodiment, the maximum upward curvature angle of the curvature portion 102 of the inserting-section cover portion 105 is 210°, and the maximum rightward curvature angle is 100°. Accordingly, the inward radius of curvature $\underline{R}$ of the curvature portion 102 is about 6 mm.

The forward-end rigid portion 107 has a diameter thereof of about 10 mm. The forward-end rigid portion 107 has a forward end surface thereof which is formed therein with an opening which is in communication with the gas feeding and water feeding channel. The cover tube 106 which is connected in a water tight manner to the forward-end rigid portion 107 has a diameter thereof which is also about 10 mm. The cover tube 106 is formed of a resinous material which has flexibility which is low in sliding frictional resistance. In the cover tube 106, the curvature portion 102 has the highest flexibility.

The cover tube 106 is formed therein with an inserting-section conduit 109 and a forceps conduit 109 in which the inserting section 111 of the endoscope and forceps channel tube 103 for inserting forceps as a piece of treatment equipment are arranged. The forceps conduit 109 which is formed within the inserting-section cover portion 105 has a diameter thereof which is formed slightly larger than a diameter of the forceps channel tube 103. The forceps channel tube 103 is made by the use of a PTFE tube which is low in sliding frictional resistance. For example, the forceps channel tube 103 has an internal bore of 2.0 mm. Steel wires are wound around the periphery of the channel tube 103. Furthermore, since the steel wires are also wound around the curvature portion 102, there is no case where the forceps channel tube 103 is tightened at the curvature portion 102 when the forceps channel tube 103 is curved.

Figure 14:
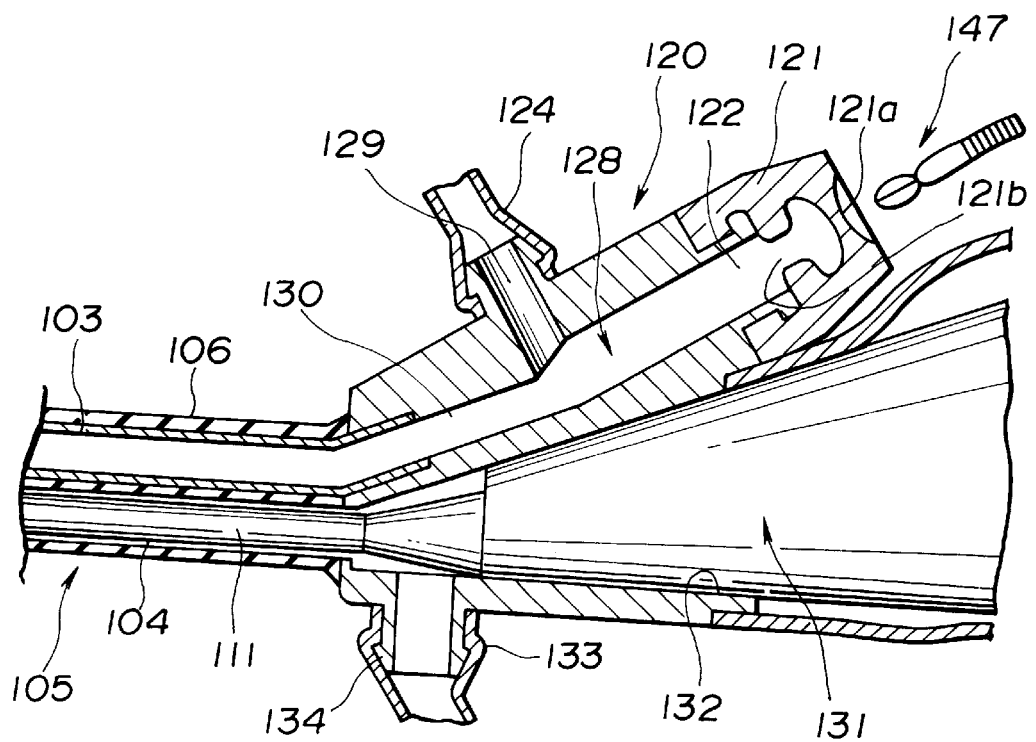

As shown in FIG. 14, the forceps channel tube 103 is in communication with a suction channel 129 which is formed in a port 120. The suction channel 129 is connected to a suction unit (not shown) through a suction tube 124. For this reason, it is possible to suck liquid, together with air, from the forward end of the inserting-section cover portion 101 by the forceps channel tube 103. Thus, the forceps channel tube 103 is sometimes called "suction channel tube".

The curvature portion 113 of the endoscope inserting section 111 is formed by a synthetic resinous tube such as a silicon rubber tube whose thickness is 0.5 mm, for example. The endoscope inserting section 111 has a so-called flex formed by a steel wire tube which is wound helically, and a net tube in which a fine wire is wound around the flex in the form of a mesh. A synthetic resinous tube such as an urethane tube low in sliding friction is arranged around the steel wire tube. The endoscope inserting section 111 is substantially in the form of an elliptical cross-section, and occupies about half of the cross-sectional area of the inserting cover portion 101.

A forceps inlet channel 128 having a forceps inlet opening 122 is formed on the port 120. The forceps inlet opening 122 is formed by a flexible material provided with a central slit 121*a* and a central bore 121*b*, and is closed by a forceps plug 121. The forceps inlet channel 128 is in communication with the suction channel 129 and a forceps guide channel 130. The forceps guide channel 130 is in communication with the forceps channel tube 103. The forceps channel 128 has a diameter thereof which is slightly larger than a diameter of the forceps channel tube 103, or a diameter of the forceps guide channel 130. The forceps channel 128 is formed in inclination with respect to a longitudinal axis direction of the inserting-section cover 105 by an angle of 30 degrees or 45 degrees. In this connection, a diameter of the suction channel 129 is substantially equal to the diameter of the forceps channel tube 103.

An operating section 131 of the endoscope has a forward end thereof which is formed with a taper. An operating-section inserting opening 132 which is formed in the port 120 of the endoscope cover is detachably inserted into the side of the forward end of the operating section 131.

A step is formed at a junction between the operating section 131 and the inserting section 111 of the endoscope. A space is defined between the port 120 of the endoscope cover and the endoscope. An inserting-section channel 104 is in communication with the space. The port 120 is provided with a nipple 134. An expansion or extension tube 133 is connected to the nipple 134 so that the expansion tube 133 is in communication with an inflator (not shown).

The port 120 is formed by synthetic resin low in sliding frictional coefficient, such as general purpose engineering plastics, and is formed such that a forceps 147 which is made of metal or synthetic resin is smoothly inserted into the forceps inlet channel 128 and the forceps guide conduit 130.

An end of the forceps channel tube 103 on the side of hand is fixedly secured to the forceps conduit 130 in a liquid tight manner by epoxy adhesive resin over a length of about 10 mm. In this connection, a surface of the forceps channel tube 103 is chemically treated so that an adhesive force is strengthened. Further, an end of the cover tube 106 is also welded or melted in a water tight manner to an end surface of the port 120 so that flexibility of the cover tube 106 which extends only 100 mm from the melted end is formed as to be improved or heightened. Accordingly, the cover tube 106 is difficult to be bent or curved at a junction between the port 120 and the forward end of the cover tube.

The relationship between the forceps for the reusable type endoscope and the endoscope cover will be described with reference to FIGS. 15A to 15D.

The forceps channel which is formed by the forceps channel tube 103, the forceps guide conduit 130 and the forceps inlet channel 128 has a length L1 which is shorter than a length L2 of an inserting portion of the forceps 147. In other words, the sum of the length (about 50 mm) of the forward end portion of the forceps which projects from the forward-end rigid portion 107 and the length (150 mm to 350 mm) of a portion of the forceps, on the side of hand, which is required to operate the forceps is about 200 mm to 400 mm.

The forceps channel has an inner diameter thereof which is formed larger by about 0.2 mm to 0.4 mm than the maximum outer diameter of the forceps which is used most frequently. The forceps channel must generally be formed to have an inner diameter which is as larger as possible. However, since the forceps channel is formed by a material having a sufficiently high mechanical strength and a low sliding friction, a forceps having an outer diameter thereof which is larger than the maximum outer diameter of the forceps channel can also be used in the forceps channel. For this reason, the forceps is smoothly inserted into the forceps channel 103 by the use of a relatively low force which does not exceed 1.5 Kg when the length of the forward-end rigid portion 107 of the endoscope cover is long or high, and the curvature portion 102 is curved to the maximum curvature angle, as shown in FIG. 13.

For example, both the length of the central slit 121*a* and the length of the diameter of the central bore 121*b* which is formed in the forceps plug 121 are 1 mm larger or 0.3 mm higher, respectively, than the length of the outer diameter of the forceps which is most frequently used. In this case, it is possible to insert the forceps into the forceps channel reasonably, and it is possible to effectively prevent liquid from leaking by the use of suction. The slit 121*a* acts when the forceps is drawn out of the forceps channel and when the liquid is wiped off from the forceps. In a case where a forceps having a larger diameter is required, the forceps plug 121 is removed from the forceps inlet opening 122. In order to withstand repeated use, the forceps plug 121 is desired to be formed preferably by silicon rubber which has a tearing strength of 45 Kg/cm$^2$ under the JIS A-type tearing test.

Moreover, in order to smoothly insert and draw the forceps into and out the forceps channel, the forceps channel is formed such that no steps and no curvature portions are formed in the forceps channel. The forceps channel has an inner diameter thereof which is larger or higher 0.5 mm than the maximum diameter of the forceps. The forceps inlet channel 128 is inclined 32° with respect to a longitudinal axis of the inserting-section cover portion 105, and the forceps guide conduit 130 is inclined 10° with respect to the longitudinal axis.

The forceps channel tube 103 is formed of a material which has a sufficiently high mechanical strength, low coefficient of sliding friction and high flexibility so that it is difficult to deform the forceps channel tube 103. In the present embodiment, the forceps channel tube 103 is formed from PTFE having a thickness of 0.5 mm. Semicircular recesses each having a depth of about 0.2 mm are formed in an outer periphery at a pitch of 0.5 mm helically at the curvature portion 102. A steel wire having a diameter of 0.2 mm is wound around the curvature portion 102. The steel wire is fixedly mounted on the curvature portion 102 by thin coating of urethane resin. With the structure, the curvature portion 102 is reinforced. Even if the curvature portion 102 is curved to the maximum curvature angle so that the radius of curvature R is equal to 7 mm, a forceps channel formed thereat is difficult to be tightened.

In the present embodiment, PTFE has a tension strength of 300 Kgf/cm$^2$ and an expansion ratio of 300% under the ASTM test 638, and a durometer hardness of D55 under D2240 of the ASTM test. The forward-end rigid portion 107 is made of SUS 303. A portion of the forward-end rigid portion 107 on which the forward end of the forceps channel tube 103 is fixedly mounted has a length shorter than 5 mm. Thus, even if the curvature portion 102 of the inserting-section cover portion 101 is curved with the maximum curvature angle, it impossible to smoothly curve the forceps channel. The forceps channel tube 103 is fixedly mounted firmly on the forward-end rigid portion 107 by epoxy resinous adhesives in a liquid tight manner. The forceps outlet opening 109 has an inner diameter thereof which is the same as the inner diameter of the forceps channel tube 103. The forceps outlet opening 109 has an inner wall thereof which has a grounded or polished surface which has a roughness thereof lower than 6.3 mm and a length thereof shorter than 10 mm.

In this manner, by the fact that the disposable endoscope cover is arranged as described above, the forceps having the rigid forward end shorter than 15 cm can smoothly be inserted into the forceps channel even under a condition that the curvature portion is curved to the maximum curvature angle as shown in FIG. 13.

In connection with the above, the forceps channel tube which is provided between the forward-end rigid portion and the port can deform the forward end of the tube, and has a length thereof which is inserted 2 mm to 3 mm into the forceps outlet opening formed in the forward-end rigid portion. Thus, even if the rigid forward end of the forceps is in contact with the inner wall of the forceps channel during inserting operation, the tube is not elongated or strengthened.

In the present embodiment, since a plurality of forcepses which have been developed to be used in the ordinary or normal reusable type endoscope and which have different lengths, outer diameters and shapes or configurations are used, the forceps channel of the disposable endoscope cover is formed in the following modes in accordance with organs to be treated and corresponding treatments.

TABLE 1

| Organs | Forceps | | Forceps Channel | |
| --- | --- | --- | --- | --- |
| | L 2 mm | Outer diameter mm | L 1 mm | Inner diameter mm |
| Stomach | Biopsy Forceps 1550 | 2.6 | 1030 | 2.8 |
| | Grasping Forceps 1650 | 3.3 | 1030 | 3.7 |
| Duodenum | Diathernary Wire Cutter 1900 | 1.8 | 1030 | 2.0 |

TABLE 1-continued

| Organs | Forceps | | Forceps Channel | |
| --- | --- | --- | --- | --- |
| | L 2 mm | Outer diameter mm | L 1 mm | Inner diameter mm |
| | Diathernary Coagulator 1900 | 1.8 | 1300 | 2.0 |
| Lleum | Grasping Forceps 1650 | 3.4 | 1350 | 3.7 |

Figure 15A:
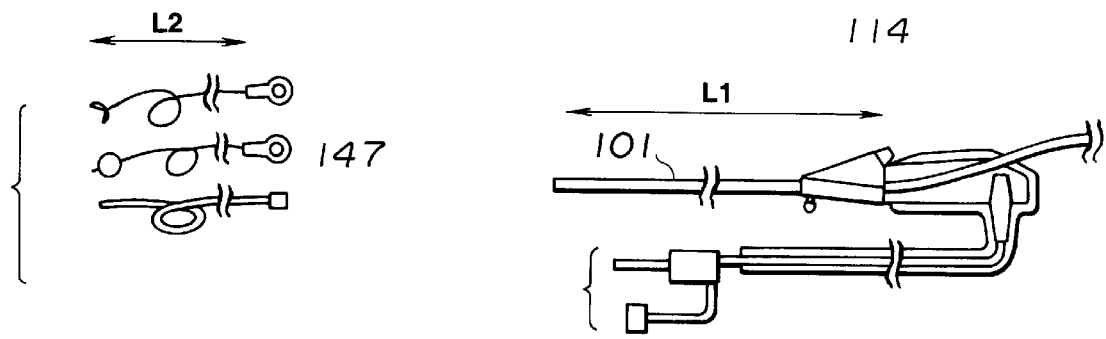
FIGS. 15(A) to 15(D) are explanatory views showing the relationship between a forceps for the reusable type endoscope and an endoscope cover.

As shown in FIG. 15A, in a case where the upper forceps 147 which has an outer diameter of 2.4 mm to 2.6 mm and a length L2 of 1550 mm to 1650 mm is used with respect to the esophagus, the stomach and the duodenum, a disposable endoscope cover may be used which has a forceps channel whose length L1 is 1330 mm and whose inner diameter is 2.8 mm.

Figure 15B:
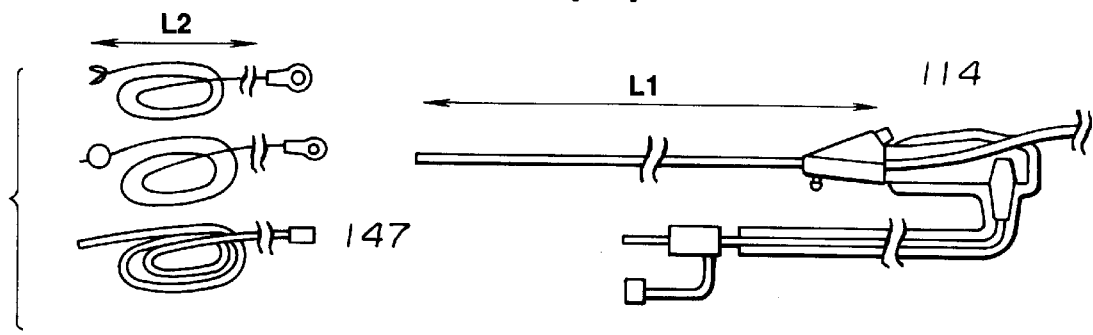

Furthermore, as shown in FIG. 15B, in a case where the upper forceps 147 which has an outer diameter of 3.3 mm to 35 mm and a length L2 of 1650 mm is used with respect to the ileum, a disposable endoscope cover may be used which has a forceps channel whose length L1 is 1350 mm and whose inner diameter is 3.7 mm.

Figure 15C:
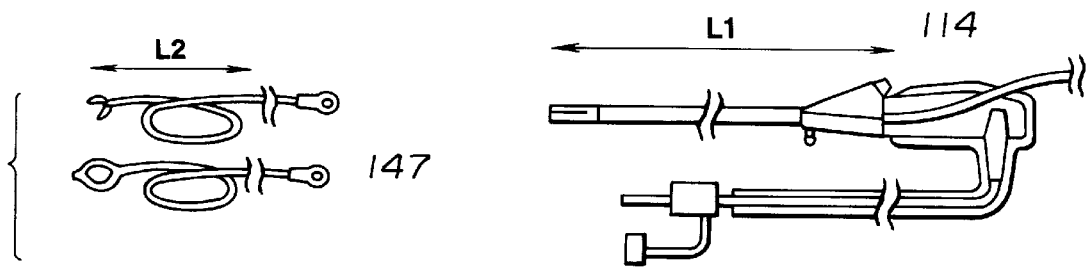

As shown in FIG. 15C, in a case where a forceps which has an outer diameter of 3.3 mm and a length L2 of 1550 mm to 1650 mm is used with respect to the stomach, a disposable endoscope cover may be used which has a forceps channel whose length L1 is 1350 mm and whose inner diameter is 3.7 mm.

Figure 15D:
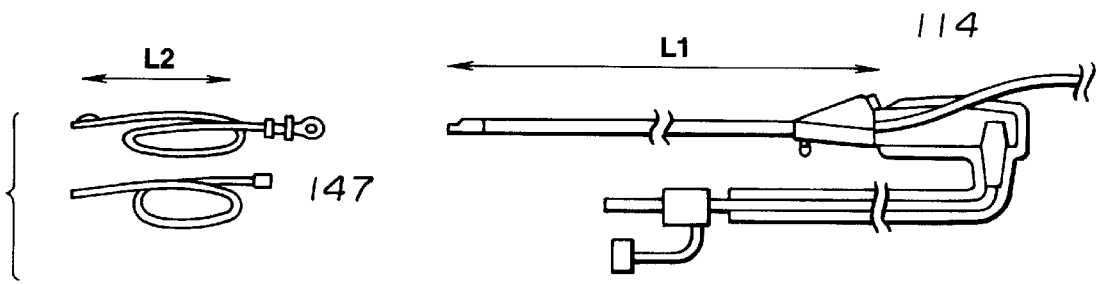

Further, as shown in FIG. 15D, in a case where a forceps which has an outer diameter of 1.8 mm and a length L2 of 1800 mm to 2000 mm is used with respect to the duodenum, a disposable endoscope cover may be used which has a forceps channel whose length L1 is 1330 mm and whose inner diameter is 2.0 mm.

In order to easily establish the relationship between the forceps and the endoscope cover, the forceps and the covers which belong to the same group may be color-coded. Moreover, a forceps channel may be provided such that the forceps channel is located inside when the endoscope cover is curved. Furthermore, the arrangement may be such that it is unnecessary to form the curvature portion 102 of the endoscope cover such that the curvature portion is curved into a circle, but the curvature of the curvature portion is gradually reduced toward the forward-end rigid portion 107 so that the forceps can easily be inserted. Further, the forceps channel tube 103 may be reinforced at the junction to the port 120, or may be provided with a steel wire so as to be reinforced over the entire length.

In connection with the above, the endoscope may be of a fiber scope type, or may be provided with a plurality of forceps channels. Moreover, combination of the forceps and the endoscope cover should not be limited to one described above, but may be one modified in various modes. For example, it is needless to say that the endoscope cover may be so arranged as to be used together with forcepses which are developed for bladder organs, respiratory organs, gynecology or the like.

As described above, according to the present embodiment, an operator can use many forcepses which are developed for a usual or normal reusable type endoscope in an endoscope system which includes an endoscope cover. For this reason, it is not required to prepare a completely new forceps which is to be developed or has been developed so as to be used only in the reusable type endoscope. Further, in a case where forceps are used in an endoscope system which includes an endoscope cover, it is possible to easily prepare the forceps, and it is possible to prevent an erroneous use of the forceps. Moreover, it is possible that the operator can use forceps which is normally or usually used. Therefore, it is possible to effectively carry treatment into practice. The other advantages are similar to those of the aforesaid embodiment.

An optical system of the cover type endoscope will next be described with reference to FIGS. 16 to 18(D).

Figure 16:
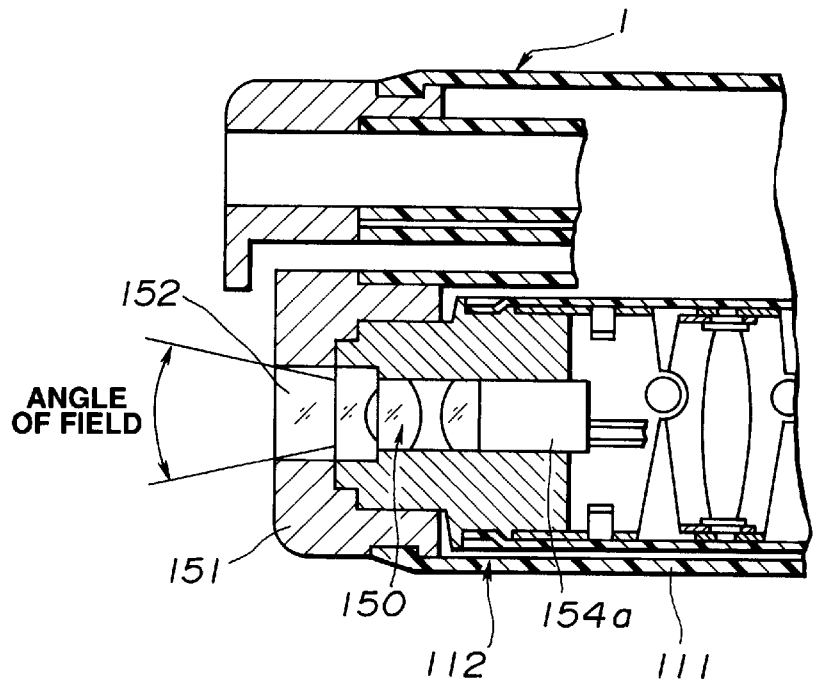

In a case of an endoscope on which the endoscope cover 1 is mounted, generally, as shown in FIG. 16, an observation optical system 150 which is arranged at a forward end 112 of a covering endoscope 111 has such disadvantages that a field of view is rejected only by a portion corresponding to a thickness of a forward end 151 of the endoscope cover 1 so that a field of viewing angle is narrowed or reduced. In view of this, in the present embodiment, a cover type endoscope will be described which is arranged such that there can be produced a field of view similar to that of a reusable type endoscope which does not require the endoscope cover 1, and which is so arranged as to be used unconsciously by an operator as a cover type endoscope.

Figure 18A:
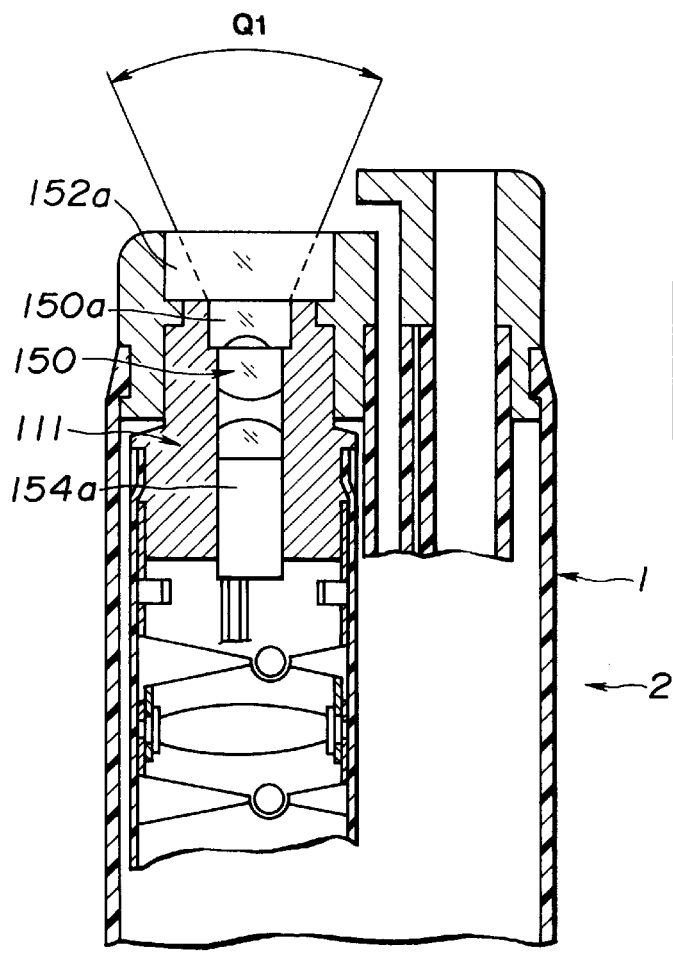
FIGS. 18(A) to 18(D) are explanatory views showing the relationship between an arrangement of the endoscope and a monitor display image plane.
Figure 18C:
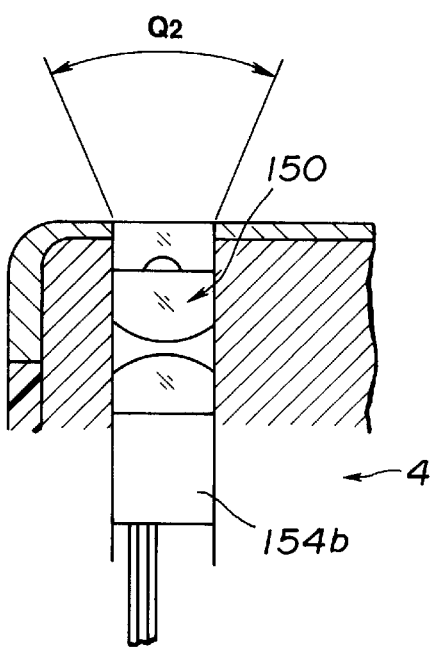

As shown in FIG. 18(A), a lens cover 152a which is arranged at a forward end of the endoscope cover 1 is larger than an outer diameter of an observation optical system 150 of the covering endoscope 111 so as to produce an angle of view Q1 so that the angle of view Q1 is brought close to an angle of view Q2 of a reusable type endoscope illustrated in FIG. 18(C). Further, a lens cover which is positioned at a front surface of an illuminating optical system is formed to be large so as to sufficiently produce luminous intensity distribution characteristics, whereby it is possible to produce advantages similar to those of the observation optical system.

Figure 17A:
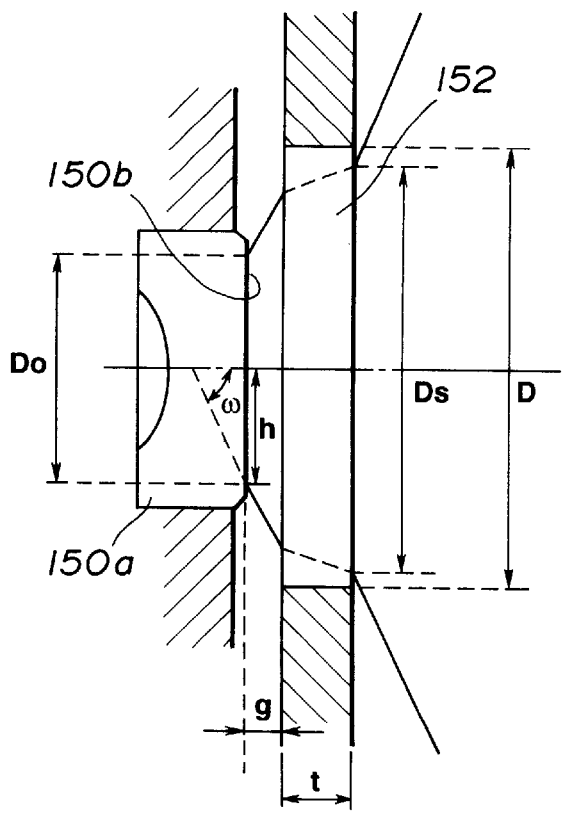
FIGS. 17(A) and 17(B) are explanatory views showing the relationship between an optical system of the cover type endoscope and a field of view.

Specifically, as shown in FIG. 17(A), in a forward-end lens 150a of the observation optical system 150, it is assumed that the maximum ray height of a first plane 150b of the forward-end lens 150a is (h=D0/2), a half angle of view is ω, a wall thickness of a lens cover 152 is $\underline{t}$, an outer diameter thereof is $\underline{D}$, a gap between the first plane 150b of the forward-end lens 150a and the lens cover 152 is $\underline{g}$, and a refractive index of the lens cover 152 is $\underline{n}$.

Then, the necessary minimum diameter DS of the lens cover 152 is expressed by the following equation.

Figure 17B:
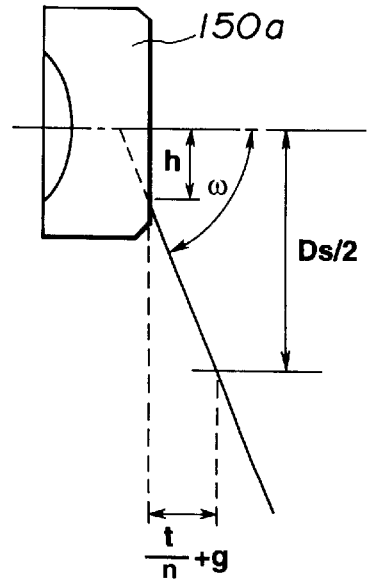

First, an optical distance of a cover glass of the lens cover 152 can be converted as an air layer of a distance t/n. Accordingly, it can be supposed as being a distance (t/n+g) as shown in FIG. 17(B) from the first plane 150b to an outer surface of the lens cover 152.

Accordingly, the necessary minimum outer diameter DS of the lens cover 152 illustrated in FIG. 17(A) can be expressed by the following equation:

$$DS=2\times\tan\omega\cdot(t/n+g)+2h=2\{\tan\omega\cdot(t/n+g)+h\}$$

That is, $$DS\geq 2\{\tan\omega\cdot(t/n+g)+h\}$$

whereby it is possible to secure the angle of view only at the covering endoscope 111 when the endoscope cover 1 is mounted.

For example, it is assumed that, when the endoscope cover 1 is mounted on the covering endoscope 111 in which an angle of view is 100° and the maximum ray height h of the first plane 150b is 1 mm, the gap $\underline{g}$ between the first plane 150b and the lens cover 152 is 0.5 mm, the wall thickness $\underline{t}$ of the lens cover 152 is 0.5 mm, and the refractive index $\underline{n}$ is 1.51633.

Then, the necessary minimum lens outer diameter DS of the lens cover 152 is as follows:

$$DS\geq 2\{\tan\omega\cdot(t/n+g)+h\}$$

$$DS\geq\{\tan 100/2\cdot(0.5/1.51633+0.5+1)\} DS>6.34$$

The outer diameter of the lens cover 152 is required to be equal to or more than 6.34 mm.

In connection with the above, the above-described relationship or relational expression is similarly held even in an endoscope system which has an angle of view unique for a covering endoscope.

Moreover, in a case of being applied to an illumination cover glass, if calculation or computation is performed at a rank or grade at which an angle α, for example, 1° to 10°, is added to a half angle of view ω, it is possible to produce sufficient luminous intensity distribution.

Specifically, it is assumed that a ray height of the first plane of the illuminating lens is hL, various wall thicknesses of the illuminating window are tL, the refractive index is nL, and the gap between the lens cover and the first plane is gL.

Then, an outer diameter DL of the illuminating lens cover is indicated as follows:

$$DL=2\{\tan(\omega+\alpha)\cdot(tL/n+gL)+hL\}$$

By satisfying the above-described relational expression, the cover type endoscope and the reusable type endoscope can produce the same observation image.

Figure 18B:
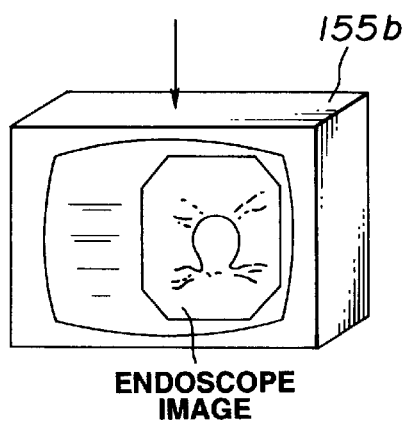
Figure 18D:
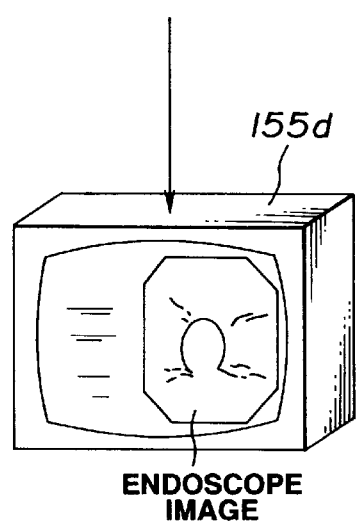

Furthermore, in the present embodiment, as shown in FIGS. 18(A) to 18(D), a similar image-plane arrangement can be produced by both the cover type endoscope and the reusable type endoscope. Specifically, as shown in FIGS. 18(B) and 18(D), an endoscope image of the cover type endoscope and an endoscope image of the reusable type endoscope are similarly displayed on monitors 155b and 155d. Thus, the present embodiment becomes an arrangement in which there is no feeling of physical disorder in a manner of visual sense.

In connection with the above, in a case where image areas of an image-pickup element are equalized in the covering endoscope and the reusable type endoscope, the forward end of the covering endoscope increases in diameter only be an observation window. Accordingly, the observation optical system of the covering endoscope is advantageous in that an incident pupil diameter is reduced, and the ray height of the incident first plane is reduced less than that of the observation optical system of the reusable type endoscope.

An arrangement of an ocular portion of a cover type fiber scope and an arrangement of an ocular portion of a reuse type fiber scope will be described with reference to FIGS. 19(A) and 19(B).

FIG. 19(A) shows a configuration or shape of a subject image and an observation scope or range which are seen when the ocular portion of the reusable type fiber scope is viewed. The reference numeral 156 in FIG. 19(A) denotes a mask element which forms a field-of-view produced through the observation optical system and the image guide. The mask element 156 is one which is arranged between the observation optical system and the ocular portion, and is arranged in the neighborhood of an ocular optical system, for example. The mask element 156 covers a peripheral portion apt generally to become dark of the field-of-view substantially in circle, and forms a confirmation index portion 156a which is, for example, substantially triangular, which partially projects inwardly of the circle such that the relationship of upper and lower positions of the mask element 156 can be confirmed. In this connection, the present embodiment is arranged such that the ocular portion of the reusable type fiber scope and the ocular portion of the cover type fiber scope have the same observation field-of-view. Accordingly, as shown in FIG. 19(B), an endoscope image observed by the ocular portion of the cover type fiber scope becomes also similar to an endoscope image observed by the ocular portion of the reusable type fiber scope.

Image processing in a video processor when the cover type endoscope or the reusable type endoscope is used in a system will next be described with reference to FIGS. 20 to 23.

FIG. 20 shows a system where the reusable type electronic endoscope 4 of concurrent image-pickup system is used. The reusable type electronic endoscope 4 is connected to a video processor (8) (not shown).

A color mosaic filter is arranged on a front surface of an image-pickup element 154b of the endoscope. A subject image imaged on an objective optical system 150b of the reusable type endoscope 4 is photoelectrically converted by the image pickup element 154b. An electric signal which is photoelectrically converted by the image pickup element 154b is image processed by a process circuit 161 of a video processor and, thereafter, is sent to a blanking circuit 162. The blanking circuit 162 applies masking treatment or processing to an output signal from the process circuit 161 by the mask signal from a mask-signal generating circuit 163 so that an endoscope image which is processed in mask and character information which is superimposed by a superimposing circuit (not shown) are displayed on the monitor 155d as shown in FIG. 18(D). Specifically, the endoscope image is displayed as an image plane partially under a condition shifted to one side, not a full display, while character information such as patient information is displayed on an open space.

Meanwhile, FIG. 21 shows a system when the covering electronic endoscope 2 of concurrent image pickup type is used. The covering electronic endoscope 2 is connected to a video processor.

A color mosaic filter is arranged on a front surface of an image-pickup element 150a of the covering electronic endoscope. A subject image which is imaged on the observation optical system 150a of the covering endoscope is photoelectrically converted by an image pickup element 154a. Since the covering electronic endoscope 2 is arranged such that a field-of-view is kicked by a lens cover 152a which is provided on the endoscope cover 1, it is necessary to form the lens cover 152 larger than the observation optical system 150a. However, if the lens cover 152a increases in size, a diameter of the forward end becomes extremely large. For this reason, in the present embodiment, a lens cover having a diameter thereof which is smaller than the objective optical system 150b and the image-pickup element 154b of the reusable type endoscope is used. Specifically, the observation optical system 150a of the covering endoscope 2 is smaller in diameter than the observation optical system 150b. The image-pickup element 154a having a small diameter is positioned in rear of the observation optical system 150a.

An electric signal which is photoelectrically converted by the image-pickup element 154a is image processed by a processing circuit 166 of the video processor and, thereafter, is sent to a blanking circuit 167. The blanking circuit 167 applies masking processing to an output signal from the process circuit 166, by a mask signal from a mask-signal generating circuit 168.

An endoscope image which is processed in mask by the blanking circuit 167 and the character information which is superimposed by the superimposing circuit (not shown) are displayed on the monitor 155b.

These processings are the same as the processing of the system which uses the reusable type electronic endoscope illustrated in FIG. 20. The mask-signal generating circuit 168 generates the mask signal capable of producing a mask configuration the same as that of the reusable type, to output the same. Thus, an endoscope image similar to that of the reusable type illustrated in FIG. 18(B) is displayed.

In this manner, the cover type endoscope and the reusable type endoscope are substantially the same as each other in images respectively produced. Thus, the arrangement is such that information produced from the visual sense by the reusable type endoscope system and the endoscope covering endoscope system, that is, an angle of view, cross-sectional configuration, and a mask are arranged substantially the same as each other, and the arrangement and the configuration of the endoscope image, and the character information are made similar to each other also in a case where there is superimposing.

In connection with the above, the observation optical system 150a and the observation optical system 150b, and the image-pickup element 154a and the image-pickup element 154b have been described as being articles different from each other. However, common ones may also be used.

An endoscope system will next be described with reference to FIGS. 22 and 23 when the cover type endoscope and the reusable type endoscope of surface sequential type are used.

Figure 22:
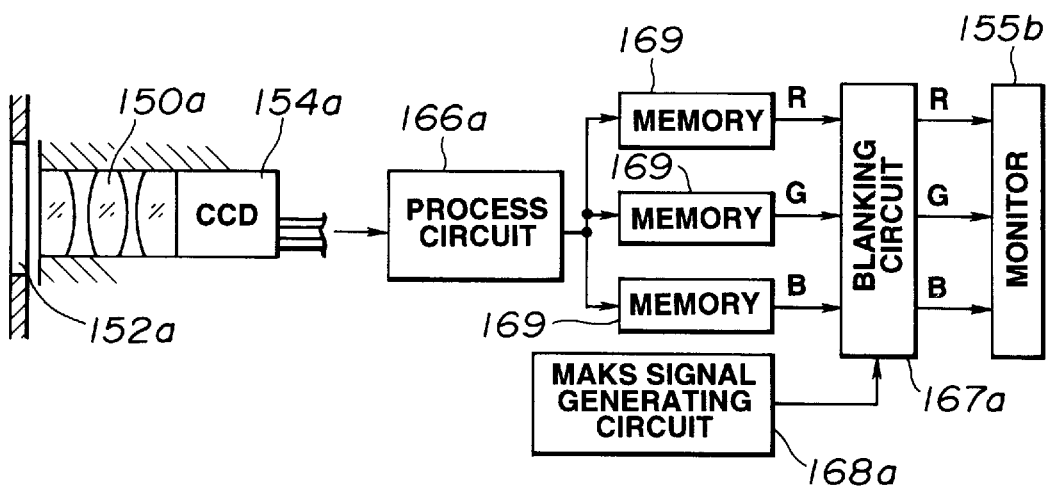
FIG. 22 is a block diagram showing signal processing in the cover type endoscope of a surface sequential image-pickup system.
Figure 23:
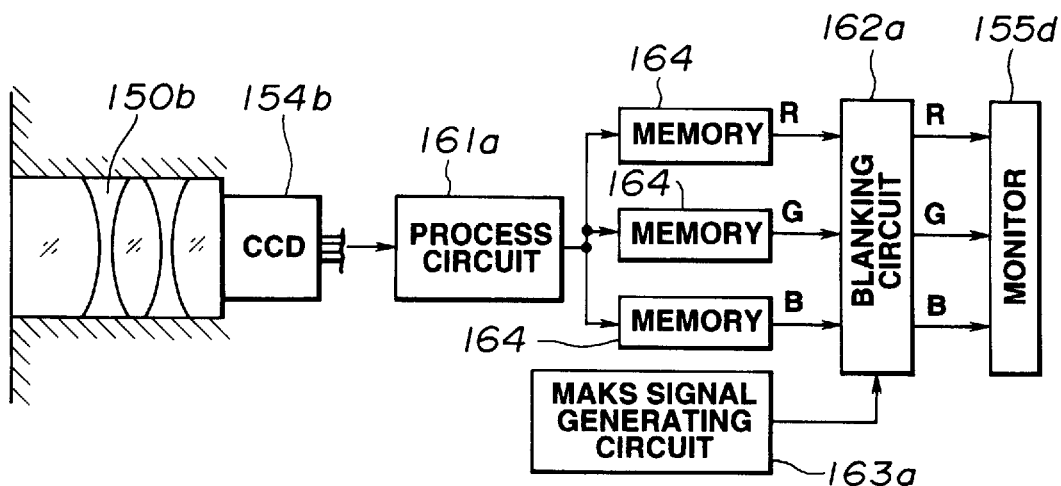
FIG. 23 is a block diagram showing signal processing in the reusable type endoscope of a surface sequential image-pickup system.

The endoscope system illustrated in FIG. 22 has a cover type endoscope, while the endoscope system illustrated in FIG. 22 has a reusable endoscope. The cover type endoscope and the reusable type endoscope are arranged such that image processing of the cover type endoscope and image processing of the reusable type endoscope perform the same or identical processing. Both the systems emit a surface sequential illuminating light by a light source unit.

At this time, electric signals corresponding respectively to R (red), G (green) and B (blue) which are produced by the image-pickup element 154b of the reusable type endoscope pass through a processing circuit 161a, and is concurred by a memory 164 for R, G and B. Operation of each of a blanking circuit 162a and the mask-signal generating circuit 163a is similar to that of the concurrent system.

Meanwhile, the electric signals corresponding respectively to R (red), G (green) and B (blue) which are produced by the image pickup element 154a of the cover type endoscope pass through a processing circuit 166a, and are concurred by memories 169 for R, G and B. Operation of each of a blanking circuit 167a and a mask-signal generating circuit 168a are similar to those of the concurrent type.

Here, although the mask processing is performed as being common to both, the arrangement may be as follows. That is, a processing switching unit is separately provided so as to convert such that images are different from each other, or an observation image is displayed in full image plane on the entire or whole monitor.

Figure 24:
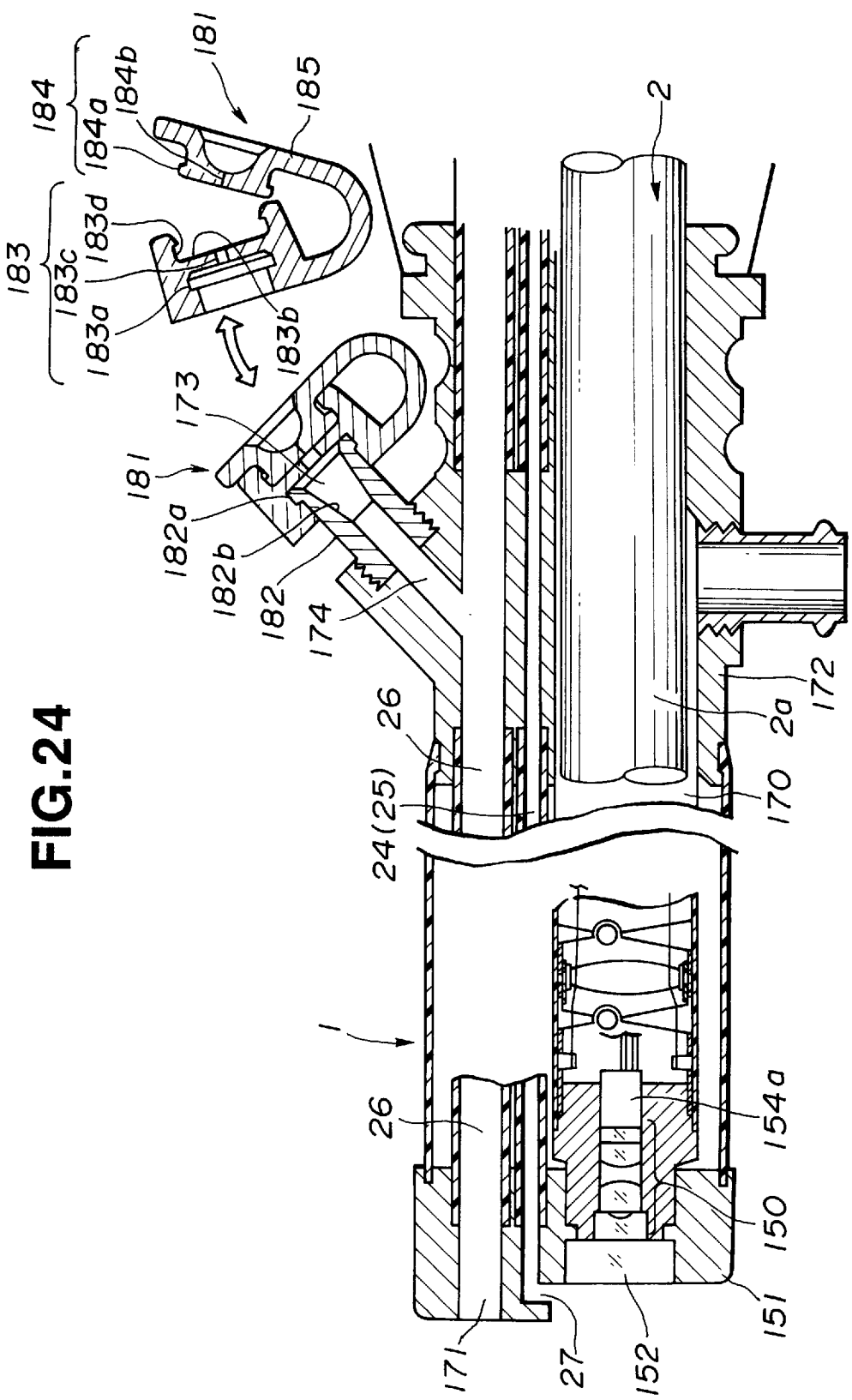
FIG. 24 is a cross-sectional view describing an arrangement of a forceps plug which is detachable with respect to an endoscope cover.

As shown in FIG. 24, an endoscope inserting channel 170 is formed within an inserting-section cover 30 of the endoscope cover 1. The inserting section 2a of the covering electronic endoscope 2 is inserted into the endoscope inserting channel 170. The gas feeding and water feeding nozzle 27 is in communication with the gas feeding channel 24 and the water feeding channel 25. Moreover, the suction channel 26 has forward end thereof which is in communication with an opening 171 in the forward-end rigid portion 151. The suction channel 26 has an intermediate portion thereof which is connected to a forceps channel 174 which is in communication with a forceps inlet opening 173 provided in a connecting element 172. The suction channel 26 has a rearward end (not shown) thereof which is connected to a fluid control unit. These channels are arranged substantially in parallel to each other within the inserting-section cover.

The forceps inlet opening 173 which is in communication with the forceps channel 26 is selectively closed by a forceps plug 181 which is made of flexible material. The forceps inlet opening 173 is formed by a tube 182 which is fixedly mounted on the connecting element 172. Furthermore, the tube 182 has a flange portion 182a and a tapered inner peripheral surface 182b. The forceps plug 181 is elastically or flexibly clamped with respect to the flange portion 182a of the tube 182.

The forceps plug 181 is formed by a first plug body 183, a second plug body 184, and an arm 185 for coupling or joining the first plug body 183 and the second plug body 184 to each other. The first plug body 183 has a first ring-like recess 183a. Engaged with the first ring-like recess 183a is the flange portion 182a of the tube 182 which forms the forceps inlet opening 173. The first plug body 183 has a disc 183b which has a central bore 183c having a diameter thereof smaller than a diameter of the forceps, and a second ring-like recess 183d. The plug body 184 has a flange portion 184a. The flange portion 184a is adapted to be flexibly inserted or fitted into the second ring-like recess 183d in the first plug body 183. Further, a slit 184b is formed at a central position of the plug body 184.

In a case where the forceps is inserted, the forceps (not shown) is inserted into the forceps inlet opening 173 through the slit 184b formed in the second plug body 184 and the central bore 183c in the first plug body 183. In this case, the central bore 183c is enlarged or expanded flexibly, and the forceps is firmly grasped by a forceps plug 181. In a case where it is difficult to insert the forward end of the forceps from the slit 184b, the second plug body 184 is removed from the first plug body 183 to expose the central bore 183c. Thus, it is possible to easily insert the forceps from the central bore 183c. Moreover, when an injector or syringe for supplying liquid is inserted into the forceps inlet opening 173, the forceps plug 181 is removed from the tube 182.

In this manner, since the forceps plug and the operating-portion cover of the disposable endoscope cover are formed separately from each other, it is made possible to easily replace the forceps plug even during inspection.

Furthermore, the forceps plugs can be used commonly for various disposable endoscope covers, and are prepared so as to be formed by materials which are provided with different hardnesses so that a plug having a hardness preferred by an operator can be used.

Figure 25:
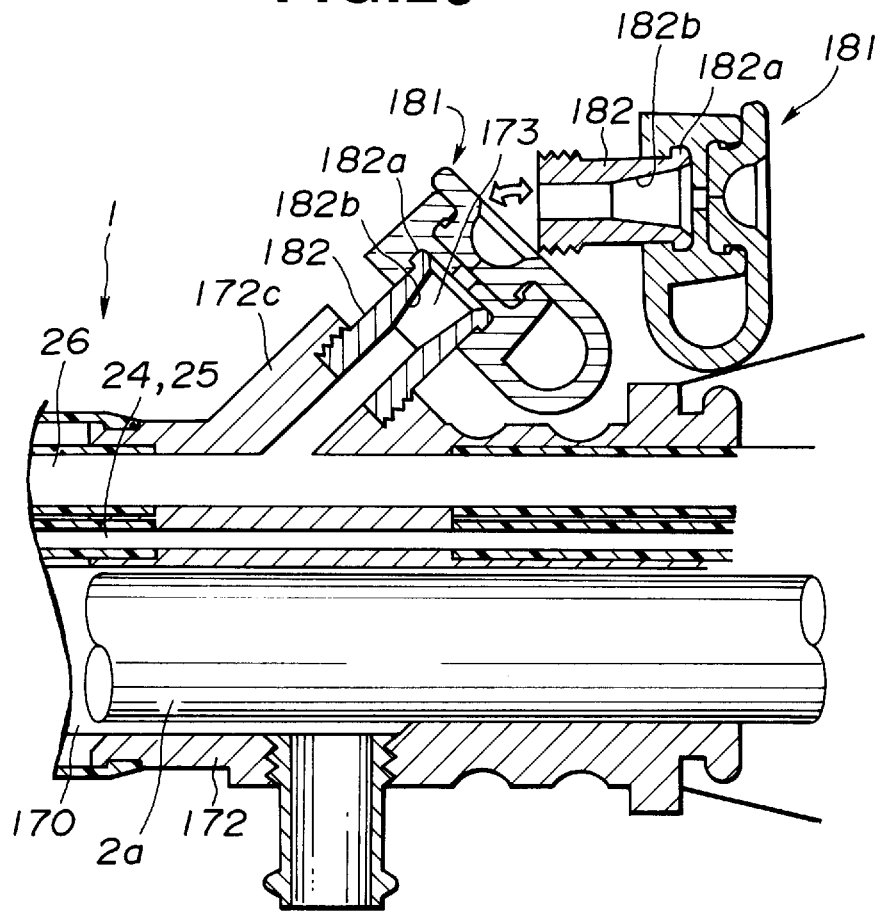
FIG. 25 is a cross-sectional view describing an arrangement of another forceps plug which is detachable with respect to an endoscope cover.

In connection with the above, as shown in FIG. 25, the arrangement may be such that the forceps plug 181 and the tube 182 which cooperate with each other to form the forceps inlet opening 173 are secured to each other and are integrated with each other so that the forceps plug 181 and the tube 182 are threadedly engaged detachably, for example, with the forceps inlet duct 172c which is formed on the connecting element 172.

Figure 26:
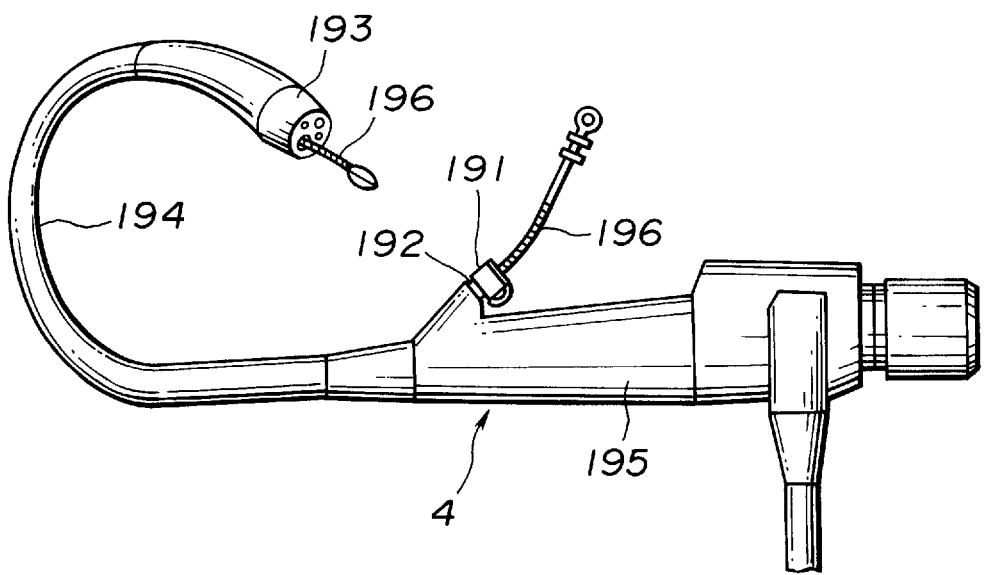
FIG. 26 is a schematic arrangement view of a reusable type endoscope which is provided with a detachable forceps plug.
Figure 27:
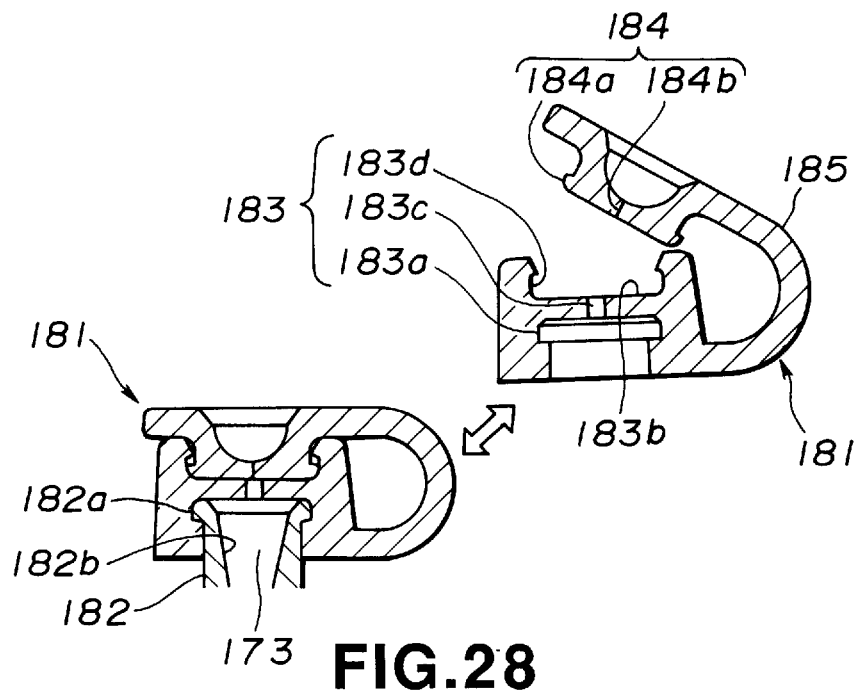
FIG. 27 is a cross-sectional view showing an arrangement of a forceps plug of a reusable type endoscope.
Figure 28:
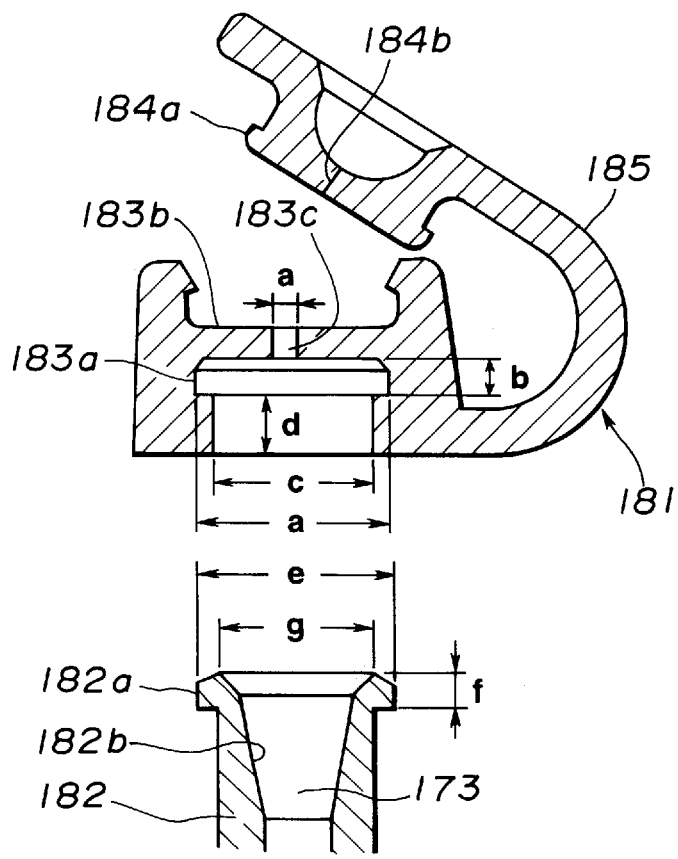
FIG. 28 is a cross-sectional view describing a dimension or size relationship of the forceps plug.

FIGS. 26 to 28 show another embodiment of the endoscope system.

In the present embodiment, a forceps plug will be described which is used to close the forceps inlet opening which is provided in the disposable endoscope cover and the reusable type endoscope.

As shown in FIG. 26, a forceps plug 191 is detachably provided on a forceps inlet opening 192 in a reusable type endoscope 190. The reusable type endoscope 190 has an inserting section 194 having a forward-end rigid portion 193, and an operating section 195. A forceps 196 which is used in the reusable type endoscope 190 is inserted into the forceps channel formed within the inserting section 194, from the forceps plug 19, and projects from the forward-end rigid portion 193. In the present embodiment, although the reusable type endoscope 190 is shown as being fiber scope type, it is needless to say that the reusable type endoscope may be an electronic endoscope.

As shown in FIG. 27, the forceps inlet opening 192 is formed by a cylindrical element 182 which has a flange portion 182a and a tapering opening 182b, similarly to FIG. 24. According to Japanese Industrial Standard (JIS) T1301, the tapering angle is $6/10$, a diameter of the central bore 183c is 1.3 mm, and a length of a slit 184b is 2.4 mm. Since a ring-like recess 183a has a diameter thereof which is formed smaller about 8% than the diameter of the flange 182a, a forceps plug 181 is firmly coupled to the cylindrical element 182. For this reason, there is no case where the forceps plug 181 comes off from the cylindrical element 182 when the forceps 196 is removed from the forceps channel. In this connection, it is preferable that the forceps plug 181 is made of silicon rubber which has a hardness of 40°±3° in accordance with JIS A-hardness.

FIG. 28 shows sizes or dimensions of various portions of a forceps plug 181. A ring-like recess 183b which is used in an ordinary or normal reusable type endoscope has a diameter a thereof which is 9.6 mm, and the recess 183b has a height b which is 1.8 mm. Sizes c and d of the forceps plug 181 are 7 mm and 3 mm, respectively. The forceps plug 181 is made of silicon rubber which has JIS A-hardness of 40°.

Meanwhile, a forceps inlet opening 173 may be formed as follows. Specifically, the flange portion 182a has a diameter e thereof which is 9.6–9.9 mm, the flange has a height f which is 1.8 mm, and the opening has a diameter g thereof which is 7.6 mm. Dimensions of the remaining portions are not defined or determined. Further, the cylindrical element 182 is made of suitable material such as, for example, plastics or metal. In the present embodiment, the inner wall 182b of the cylindrical element is tapered so that the syringe can easily and reliably be secured to the cylindrical element.

In this manner, the forceps plug 181 can be used in common to the reusable type endoscope and the disposable protective cover. Accordingly, it is possible to selectively and easily use the forceps plug.

FIGS. 29 to 33 show another embodiment of the present invention.

Figure 29:
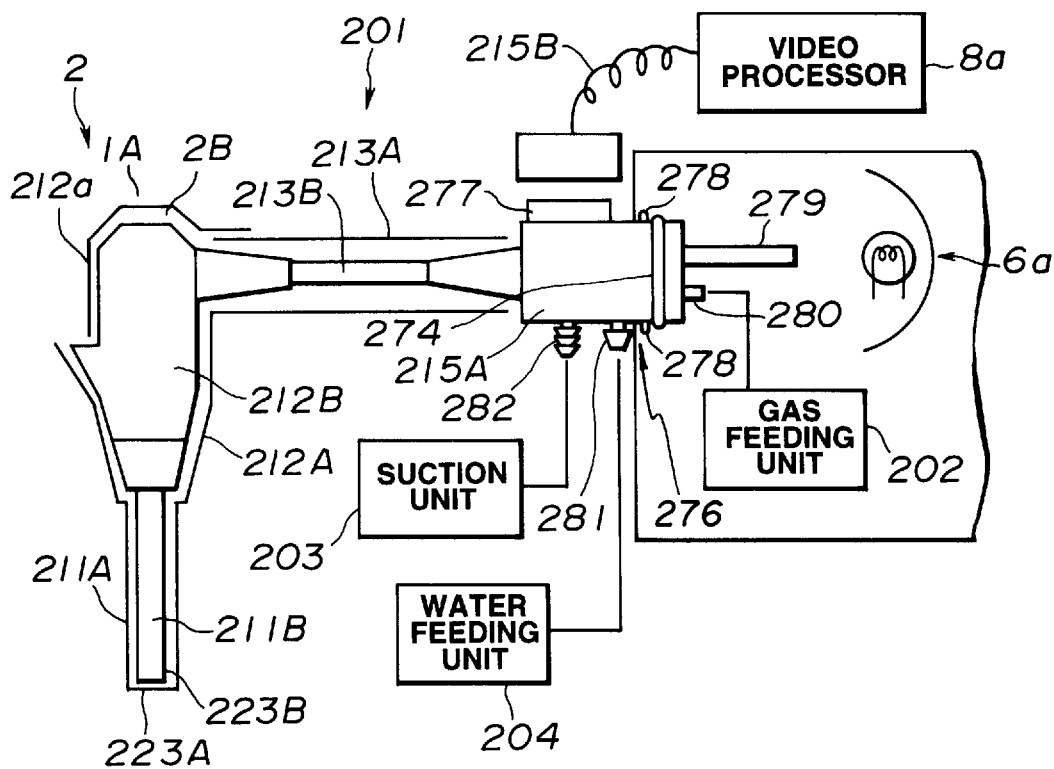
FIGS. 29 to 31 relate to a connector of an endoscope system.

An endoscope system 201 illustrated in FIG. 29 comprises a cover type endoscope 2 have a channel-less endoscope cover 1A and a covering endoscope 2B which is mounted on the channel-less endoscope cover 1A, a light source unit 6a that is a peripheral equipment for a reusable type endoscope inspection, for supplying an illuminating light to the covering endoscope 2B, a video processor 8a which performs signal processing of an image-pickup element which is built in the covering endoscope 2B, a gas feeding unit 202, a suction unit 203 and a water feeding unit 204 which are in communication respectively with a gas feeding line, a suction line and a water feeding line.

In a case where endoscope inspection is performed, use is made repeatedly in such a manner that the clean covering endoscope 2B is covered by the clean endoscope cover 1A and, after inspection, the endoscope cover 1A is discarded, while a new clean endoscope cover 1A is covered on the covering endoscope 2B.

The covering endoscope 2B comprises an elongated inserting section 211B having elasticity or flexibility, an operating section 212B which is formed on the side of a proximal end of the inserting section 211B, and a universal cord 213B which extends from a side of the operating section 212B. An observation optical system for imaging a subject image to an image-pickup element is arranged at a forward end of the inserting section 211B. A connector 215A Which is provided at a distal end of the universal cord 213B is connected to the light source unit 6a for a reusable type endoscope, whereby the illuminating light from a lamp within the light source unit is supplied to an illuminating optical system. The illuminating light passes through a cover lens (not shown) which is provided at an end surface of a cover forward end 223A of an inserting-section cover portion 211A which is arranged in opposed relation to a lens cover (not shown) at a forward end 223B of the inserting section 211B, and is outgoing toward the forward subject.

A subject image of an illuminated affected or diseased part passes through a cover observation window (not shown) provided adjacent to the cover lens cover, and an observation optical system provided on the inserting section 211B of the covering endoscope 2B which is arranged in opposed relation to the cover observation window and which is provided inside thereof, and forms an optical image on an image-pickup surface of image pickup means such as CCD or the like which is arranged on a focal plane.

The optical image imaged on the image pickup surface is photoelectrically converted and is inputted to the video processor 8a through a signal cable which is inserted into the inserting section 211B and the universal code 213B. The optical image is processed in signal and, subsequently, a standard image signal is generated. The subject image is displayed on the monitor image plane.

Meanwhile, the endoscope cover 1A is roughly divided into the inserting-section cover portion 211A which covers the inserting section 211B, the operating section 212B and the universal cord 213B of the covering endoscope 2B, an operating-section cover 212A, and a universal cord cover 213A. The arrangement is such that the inserting-section cover 211A, a part of the operating-section cover 212A and the universal cord cover 213A are formed in a united manner, and an opening formed upper the operating-section cover 212A is closed by a cover lid closure 212a.

When the endoscope cover 1A is covered over the covering endoscope 2B, the inserting section 211B of the covering endoscope 2B is inserted into the inserting-section cover portion 211A, and the universal cord 213B is inserted into the universal cord cover 213A to cover the inserting section 211B, the operating section 212B and the universal cord 213B of the covering endoscope 2B. After they have been covered in accordance with a predetermined manner, the opening in the endoscope cover 1A is closed by the cover closure 212a.

Furthermore, an engaging element 274, such as a C-ring, is provided on an end of the connector 215A. The engaging element 274 is so arranged as to be engaged with an engaging portion 276 of a connector inserting port which is provided in the light source unit 6a for a reusable type endoscope, and to be fixedly mounted on the engaging portion 276.

Further, the connector 215A is provided with a video connector 277 which is connected to a video cable 215B which transmits an image signal to the video processor 8a, an electrical contact 278 for transmitting a modulated-light electric signal from the video processor 8a, to an electric contact receptor groove 275a which is provided at the connector inserting port which transmits the modulated-light electric signal to the light source unit 6a through the video connector 277 and the signal cable, an incident portion 279 upon which an illuminating light outgoing from the light source unit 6a is caused to be incident, a gas feeding port 280 to which gas feeding for lens cleaning is performed to the forward end of the inserting section 211A of the covering endoscope 2B is connected so that the gas feeding port 280 is connected to the gas feeding unit 202, a water feeding base 281 which is connected to a water feeding line for performing water feeding from the forward end of the inserting section 211A so that the water feeding base 281 is connected to the water feeding unit 204, and a suction base 282 which is connected to a suction line for drawing unnecessary dirt from the forward end of the inserting section 211A so that the suction base 282 is connected to the suction unit 203. In this connection, the lines and wirings which are connected to the bases 281 and 282, an electrical contact 278, the incident portion 279, the gas feeding port 280 and the video connector 277 are arranged within the connector 215A.

Moreover, the light source unit 6a and the gas feeding unit 202 may be incorporated within an endoscope control unit which processes the electric signal transmitted from the covering endoscope 2B or which transmits the electric signal to the covering endoscope 2B to control the same.

Figure 30:
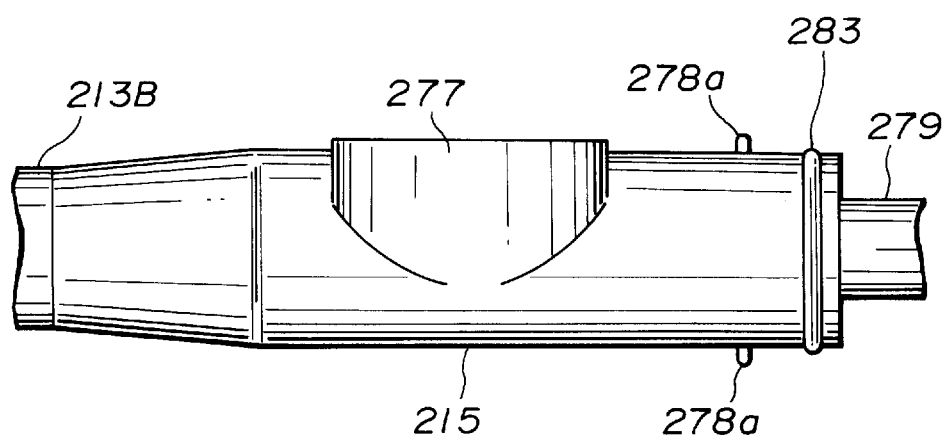

In connection with the above, as shown in FIG. 30, the covering endoscope which is used in the endoscope cover having channels is so arranged as to be connected to an external unit (light source unit or the like) which is used in the covering endoscope, by a connector 215 which is provided at a distal end of a universal cord 213B extending from the covering endoscope. In the cover type endoscope which uses an endoscope cover having channels, a forceps channel, a suction line which are in contact with the outer surface of the endoscope are provided on the side of the endoscope cover 1A. For this reason, it is possible to reduce the diameter of the connector 215 correspondingly to the fact that the gas feeding base 280, the water feeding base 281 and the suction base 282 are unnecessary or are dispensed with, as compared with the connector 215A which is provided on the channel-less endoscope covering endoscope 2B. Accordingly, it is also possible to reduce the diameter of the connector inserting port of the light source unit (not shown) for covering endoscope connecting the connector 215, as compared with that of the light source unit 6a for a reusable type endoscope. In FIG. 30, the connector 215 and the universal cord 213B are formed to have substantially the same outer diameter.

Furthermore, an engaging element 283, such as a C-ring is provided at the end of the connector 215. The arrangement is such that the engaging element 283 is engaged with an engaging portion provided at the connector inserting port which is provided in a light source unit (not shown) for endoscope covering endoscope having channels, and is fixedly mounted on the engaging portion so as to be fixed.

Further, provided on the connector 215 are the video connector 277 to which the video cable 215B is connected, an electric contact 278a for transmitting a modulated-light signal for adjusting or regulating an illuminating light quantity or intensity of a light source unit (not shown) for an endoscope covering endoscope having channels, to the light source unit for endoscope covering endoscope having channels, and the incident portion 279 upon which an illuminating light outgoing from the light source unit (not shown) for endoscope covering endoscope having channels is incident. Moreover, wiring which is connected to the electric contact 278a and the incident portion 279 is provided within the connector 215.

In this manner, since the connector 215 and the universal cord 213B are formed substantially to the same outer diameter, catching or hooking of the connector 215 is eliminated when the endoscope cover 1A is coated or covered so that insertion and removal of the universal cord 213 and the connector 215 with respect to the universal cord cover 213A are facilitated.

Here, the light source unit for endoscope covering endoscope having channels may be one which is incorporated in an endoscope control unit which processes an electric signal which is transmitted from the endoscope covering endoscope having the channels or which transmits an electric signal to the endoscope covering endoscope having channels, to control the same.

Figure 31:
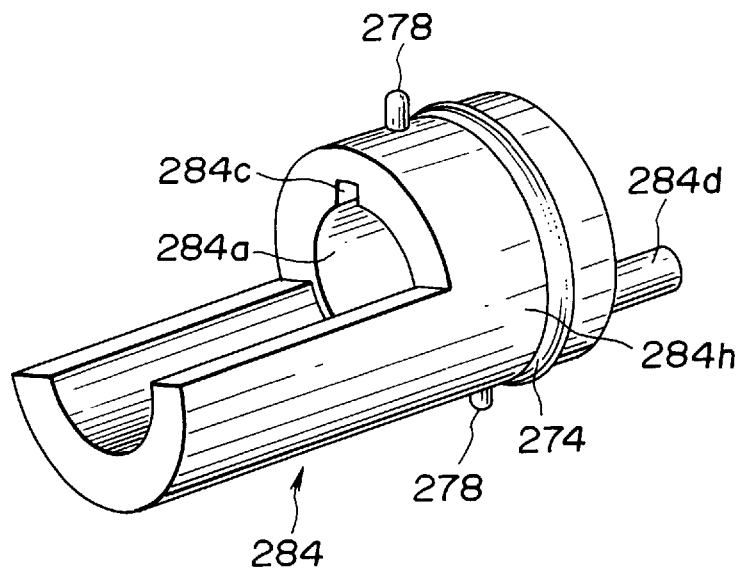
Figure 32:
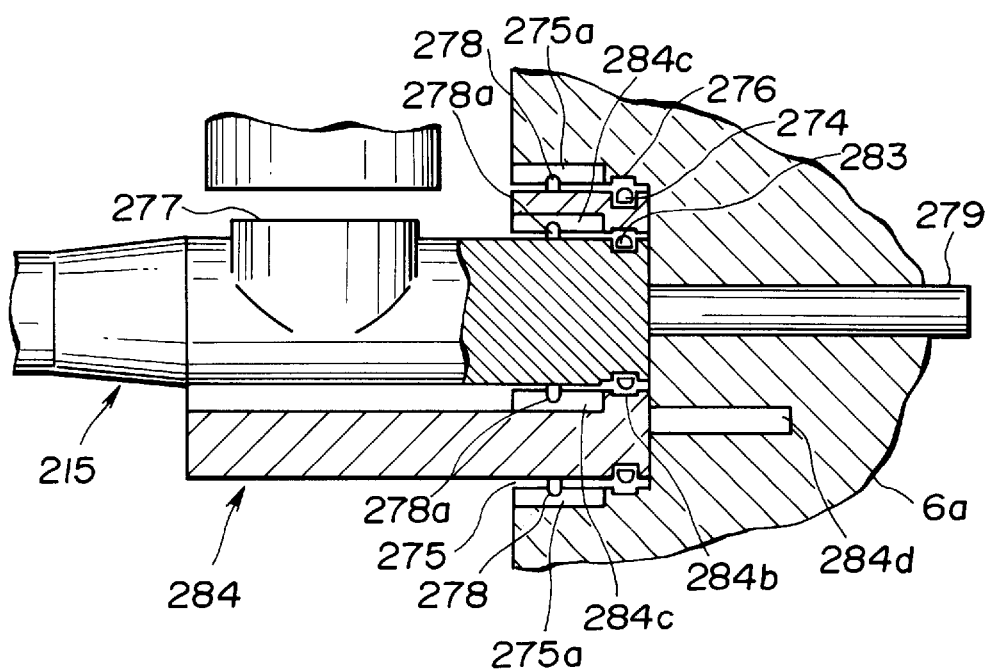
FIG. 32 is a cross-sectional view showing a condition under which the adaptor of the connector on the side of the covering endoscope is connected to a light source unit through an adaptor.

Meanwhile, the reference numeral 284 illustrated in FIG. 31 is an adaptor that is an example of an endoscope connecting element for connecting a connector 215 provided at a distal end of the universal cord 213B of the endoscope covering endoscope having channels which is used in an endoscope cover type having channels, to the connector inserting port 75 in the light source unit 6a for a reusable type endoscope.

The adaptor 284 is formed with a connector inserting port 284a that is a first connecting portion into which the connector 215 in inserted along an axial center, and a light-source-unit connecting portion 284h that is a second connecting portion in which an outer periphery of the adaptor 284 is connected to the connector inserting port which is provided in the light source unit 6a for a reusable type endoscope.

Further, the connector inserting port 284a has a deep portion which is formed with an engaging portion 284b which is engaged with the engaging element 283 provided at an end of the connector 215. Moreover, an electric contact receptor groove 284c which is connected to the electric contact 278a is formed within the connector inserting port 284a. Specifically, when the connector 215 is inserted into the connector inserting port 284a, the electric contact 278a which is provided on the outer periphery of the connector 215 is inserted into the electric contact receptor groove 284c and is conducted thereto.

Figure 33:
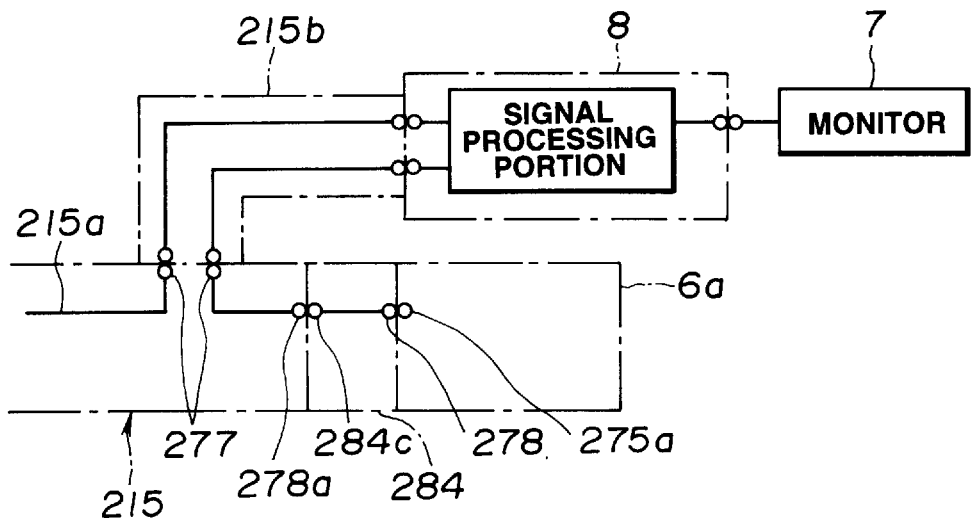
FIG. 33 is a wiring diagram showing a principal portion of the cover type endoscope system.

Furthermore, the adaptor 284 has the outer periphery thereof which is provided with the electric contact 278 which is conducted to the electric contact receptor groove 275a provided in the connector inserting port 75 of the light source unit 6a for a reusable type endoscope and which is conducted to the electric contact receptor groove 284c on the side of the adaptor 284. In this connection, wiring thereof is illustrated in FIG. 33.

The engaging element 283 of the connector 215 is engaged with the engaging portion 284b, whereby the adaptor 284 is fixedly mounted on the connector 215. Further, the adaptor 284 has an outer periphery thereof which is provided with the engaging element 283 such as a C-ring which is engaged with the engaging portion 276. Moreover, provided in projection on the end surface of the adaptor 284 is a positioning rod 284d which performs positioning when the adaptor 284 is inserted into and fixedly mounted on the connector inserting port 75 in the light source unit 6a for a reusable type endoscope. In the connection, the positioning rod 284d is provided at the same position and with the same size or dimension as the gas feeding port 280 which is provided in the connector 215A.

Function or operation of the endoscope system arranged as described above will be described.

When the connector 215 provided on a distal end of the universal cord 213B of the endoscope covering endoscope having channels which is used in the endoscope cover type endoscope having channels is connected to the light source unit 6a for a reusable type endoscope, the adaptor 284 is first mounted on the connector 215, and the adaptor 284 is fixedly mounted on the connector 215. Then, the electric contact 278a of the connector 215 is conducted to the electric contact receptor groove 284c in the adaptor 284.

Then, the light-source-unit connecting portion 284h which is provided on the outer periphery of the adaptor 284 mounted on the connector 215 is inserted into the connector inserting port 275 which is provided in the light source unit 6a for a reusable type endoscope. Then, the incident portion 279 which projects from the connector 215 is inserted into the light source unit 6a for a reusable type endoscope. Further, the positioning rod 284d is positioned and is fixed. Thus, the electric contact 278 which is conducted to the electric contact receptor groove 284c in the adaptor 284 is conducted to the electric contact receptor groove 275a which is provided on the connector inserting port 275 of the light source unit 6a for a reusable type endoscope.

As a result, it is possible to connect the connector 215 which is provided at the distal end of the universal cord 213B of the endoscope covering endoscope having channels which is used in the endoscope cover type endoscope having channels, to the light source unit 6a for a reusable type endoscope. When the endoscope covering endoscope having channels is used, a conventional light source unit can be used. Thus, a private unit is made unnecessary or is dispensed with so that the light source unit 6a becomes an economical unit which has compatibility or interchangeability.

The other arrangement of the connector of the covering endoscope will be described with reference to FIG. 34.

Figure 34:
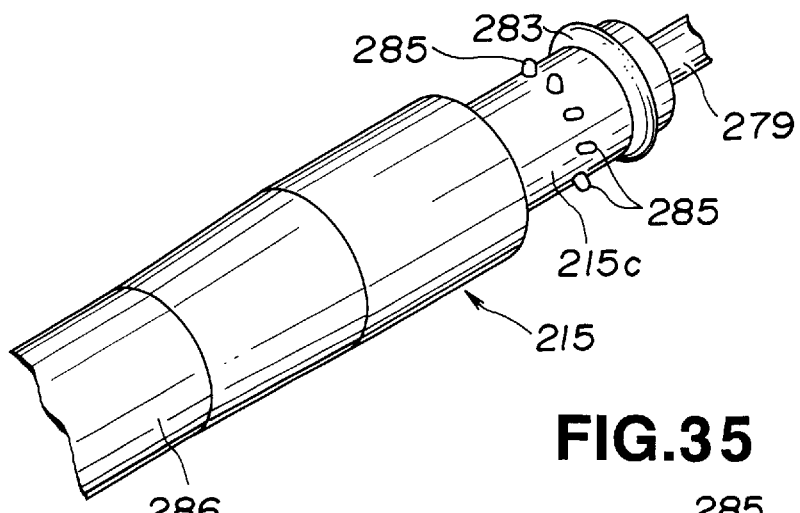
FIG. 34 is a perspective view showing a connector of the other arrangement on the side of a covering endoscope.

As shown in FIG. 34, if a step 215c is provided on a connector 215 and if video contacts 285 each having a height thereof which is contended within the outer diameter of the connector 215 are provided on the outer periphery of the step 215c, it is possible to arrange the video connector 277 of the connector 215 shown in FIG. 30 only by pins. Correspondingly, it is possible to reduce, in size, the connector 215, and it is possible to reduce a diameter of a universal cord 286 which is connected to or combined with the connector 215.

If the reduction in size of the connector 215 and the reduction in diameter of the universal cord 86 can be realized, not only the inserting operation of an engaging element 283 is provided on the step 215c is facilitated, but also a reduction in size or miniaturization of the video processor 8a can be realized.

Another arrangement of the connector of covering endoscope will be described with reference to FIG. 35.

Figure 35:
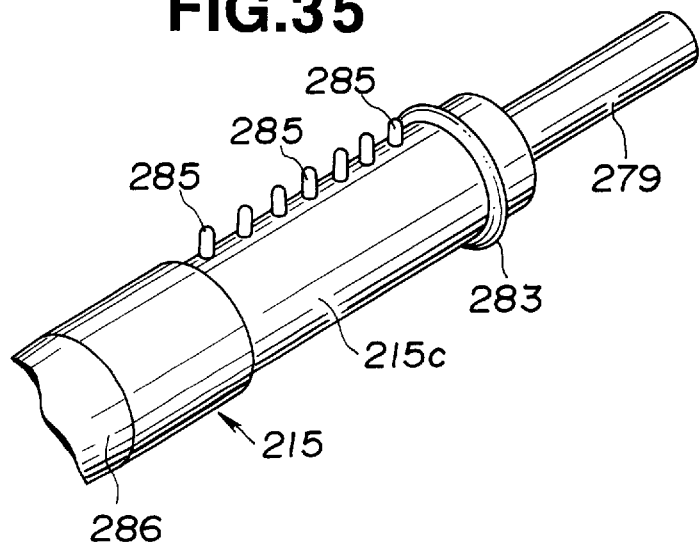
FIG. 35 is a perspective view showing a connector of the other arrangement on the side of a covering endoscope.

As shown in FIG. 35, the video contacts 285 are arranged on a connector 215 in a single row along an axial direction. If a step 215c is provided only on a portion on which the video contacts 285 are provided, it is possible to bring a projecting amount of the video contacts 285 about to half, as compared with an arrangement in which the video contacts 285 are arranged around the step 215c, as shown in FIG. 34. Accordingly, further reduction in size of the connector 215 and further reduction in diameter of a universal cord 286 can be realized.

Figure 36:
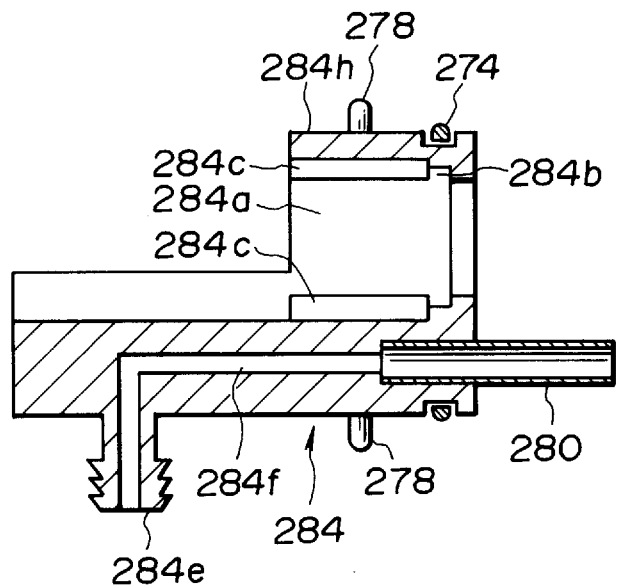
FIG. 36 is a cross-sectional view showing the other arrangement of the adaptor.

The other arrangement of the adaptor will be described with reference to FIG. 36.

In the embodiment illustrated in FIG. 31, the positioning rod 284d is provided in projection from the end surface of the adaptor 284. However, the adaptor 284 illustrated in FIG. 31 is provided with the gas feeding port 280 in place of the positioning rod 284d. A gas feeding base 284c is provided on an adaptor 284, and the gas feeding base 284e and a gas feeding port 280 are in communication with each other through a gas feeding line 284f.

In connection with the above, a gas feeding line which is provided in an endoscope cover (not shown) having channels is adapted to be connected to the gas feeding base 284e. For this reason, gas feeding from the gas feeding unit 202 is fed to the gas feeding line which is provided in the endoscope cover (not shown) having channels, through the gas feeding port 280 and the gas feeding line 284f. According to the present embodiment, since the gas feeding unit 202 can be utilized as it is, a private unit becomes unnecessary and can be dispensed with.

Another arrangement of the adaptor will be described with reference to FIGS. 37 to 39.

Figure 37:
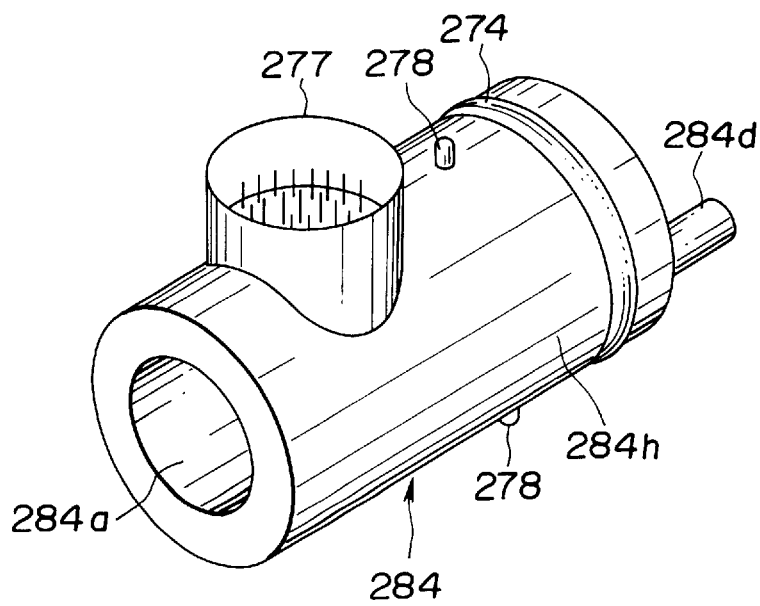
FIGS. 37 to 39 relate to an adaptor of the other arrangement.
Figure 38:
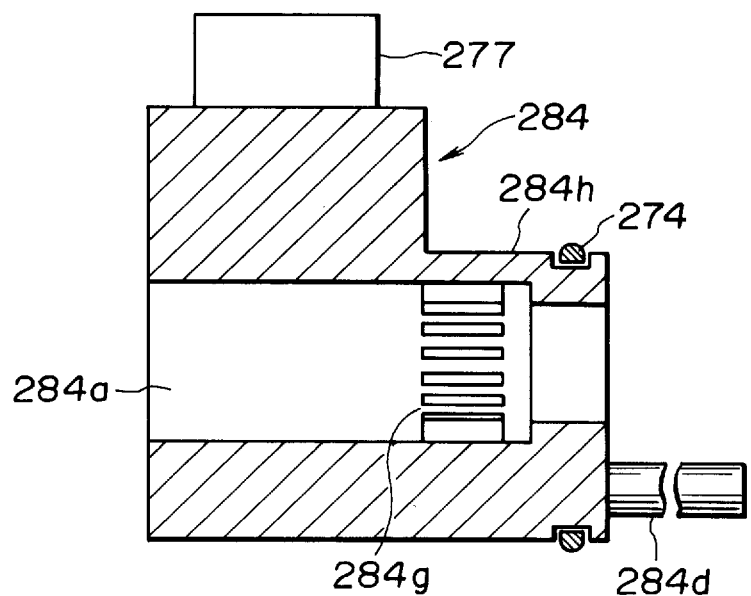
Figure 39:
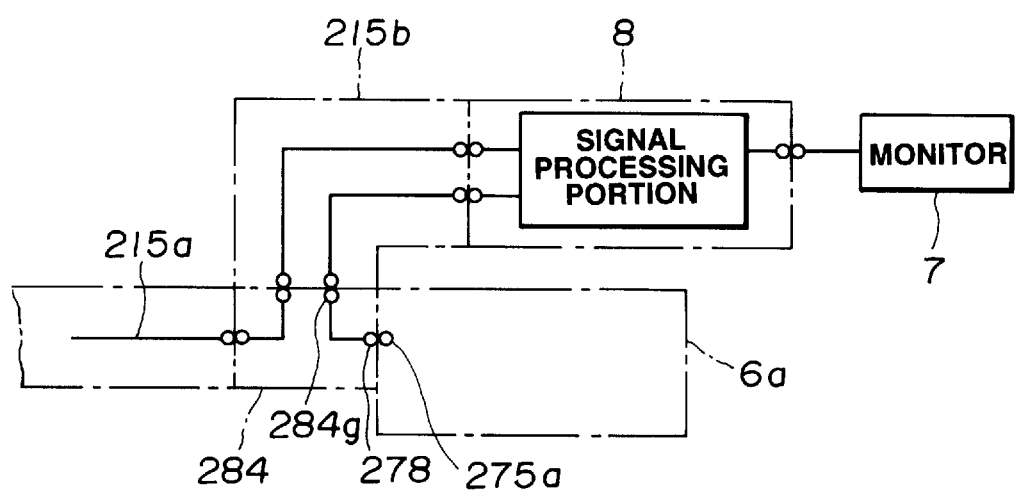

An adaptor 284 illustrated in FIGS. 37 to 39 is provided with a video connector 277 to which a video cable 215B for transmitting an image electric signal to a video processor 8a is connected, and is provided with a video contact receptor groove 284g which is conducted to the video connector 277 to receive the image electric signal, in an inner periphery of a connector inserting port 284a. The connector 215 illustrated in FIG. 34 can be mounted on and fixed to the adaptor 284.

Further, the video connector 277 and the electric contact 278 are conducted to each other so that an electric signal received by the video connector 277 is transmitted to electrical contacts 278.

When the adaptor 284 is mounted on the connector 215 illustrated in FIG. 34, a video contact 285 is fitted into and is in contact with the video contact receptor bore 84a in the adaptor 284 so that the video contact 285 and the video contact receptor groove 284a are conducted to each other.

The image electric signal which is transmitted within a covering endoscope (not shown) conducts the video contact 285 and the video contact receptor bore 284a to each other and is transmitted to the video processor 8a through the video connector 277 and the video cable 215B.

Meanwhile, the modulated-light electric signal which is sent from the video processor 8a and which is transmitted through the video connector 277 and the video cable 215B is transmitted to a light source unit 6a for a reusable type endoscope through the electric contact 278.

As a result, by the use of the adaptor 284, it is possible to connect the connector 215 to the light source unit 6a for reusable endoscope, even though the connector 215 from which the video connector 277 is removed for reduction in size or miniaturization.

In connection with the above, the video contact receptor grooves 284g which are provided in the connector inserting port 284a in the adaptor 284 may be arranged in a single line or row such that the connector 215 illustrated in FIG. 35 can be mounted.

An arrangement of the fiber scope will briefly be described with reference to FIGS. 40 and 41.

Figure 40:
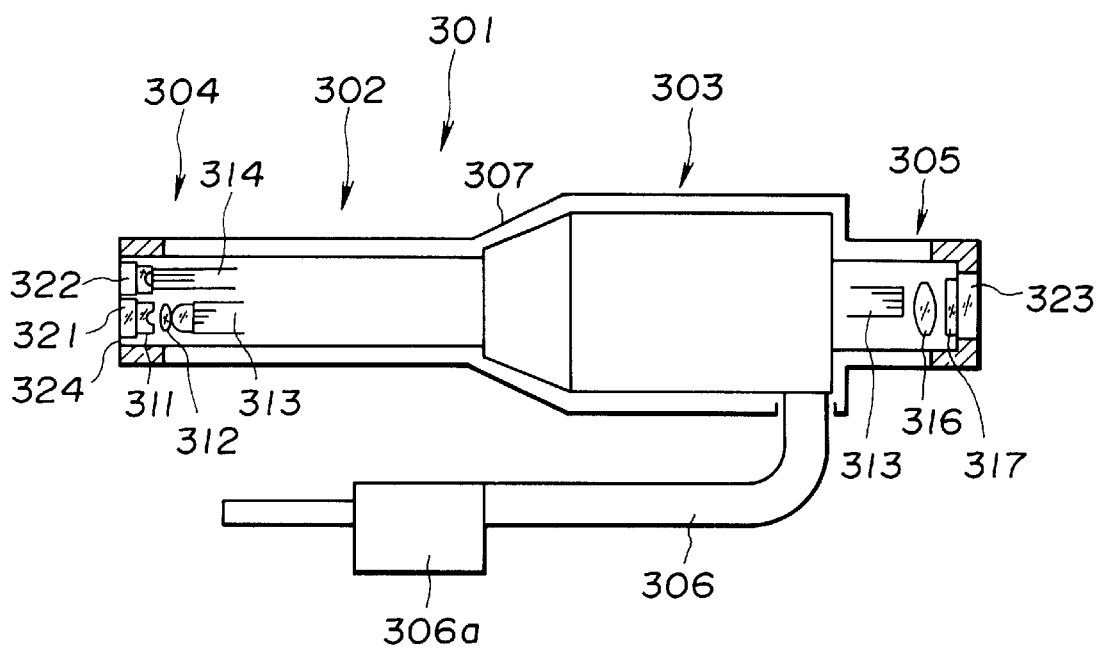
FIGS. 40 and 41 relate to an operating section of the endoscope system according to the invention.

As shown in FIG. 40, a fiber scope 301 has an elongated inserting section 302 which is inserted into a body or the like of a patient. An operating section 303 serving also as a gripper section for gripping the fiber scope 301 is provided on the side of the inserting section 302.

An observation window 311 is provided in a forward end 304 of the inserting section 302, and is arranged in opposed relation to an observation optical system 312 for observing a subject. An image guide 313 has one end thereof which is arranged on a focal plane of the observation optical system 312. Thus, the arrangement is such that a subject image can be transmitted to the side of hand. Moreover, a fiber 314 for illumination is inserted into the inserting section 302 so that an illuminating light is illuminated on the subject.

The operating section 303 is provided with an angle knob (not shown) for operating in curvature a curvature portion (not shown) of the inserting section 302. Furthermore, an ocular portion 305 is provided which has an ocular optical system 316 and an ocular window 317 for observing the subject image which is transmitted by an image guide 313.

Further, a universal cord 306 extends from a side surface of the operating section 303. The illuminating fiber 314 is provided in the universal cord 306. The universal cord 306 has a forward end thereof which is provided with a connector 306a. The arrangement is such that the connector 306a is connected to a light source unit (not shown), whereby the illuminating light is supplied.

An endoscope cover 307 which covers at least the inserting section 302, the operating section 303 and the ocular portion 305 covers such fiber scope 301 in order to prevent infection between patients.

The endoscope cover 307 has a forward end thereof which is provided with an observation lens cover 321 so that the endoscope cover 307 is positioned on an optical axis of the observation optical system 312 of the fiber scope 301. A ring-like light shielding element 324 for preventing the illuminating light from invading is arranged around the observation lens cover 321. Moreover, the endoscope cover 307 is provided with an illuminating lens cover 322 and is so arranged as to be positioned in front of the fiber scope 301. Meanwhile, a sheath ocular window 323 is provided at a position corresponding to the ocular window 317 on the side of hand of the endoscope cover 307.

The illuminating light supplied by the light source unit is irradiated from the illuminating lens cover 322 arranged on the endoscope cover, from the universal cord 306 through the operating section 303 and the inserting section 302 by the illuminating fiber 314 to illuminate the subject. A light image of the subject which is illuminated in this manner passes through the observation lens cover 321, the observation optical system 312 and the image guide 313 which are arranged on the endoscope cover and is observed by an operator through the ocular optical system 316, the ocular window 317 and the sheath ocular window 323 of the ocular portion 305.

Such endoscope cover 307 is replaced in every single case. When the endoscope cover 307 is reused after the case, the used endoscope cover is discarded and is replaced with a new endoscope cover.

As is well known, the video scope is arranged substantially similarly to the fiber scope 301. However, transmission of the observation image is performed by an electric signal through a signal line, not through the image guide 313. Specifically, the arrangement has been such that an image imaged on an image-pickup element, such as a CCD, is photoelectrically converted by an objective optical system, and the electric signal is transmitted, and signal processing is performed by a video processor (not shown) to project an observation image on a monitor.

Accordingly, an ocular portion for naked-eye observation is unnecessary and dispensed with. In a conventional video scope, a switch portion provided with a plurality of switches for controlling the video processor has been arranged at a position corresponding to the ocular portion.

Since the switch portion of the video scope has been decided in contour or form with a view to operability of the switch, the switch portion has been different in form from the ocular portion 305 of the fiber scope 301. For this reason, even if an attempt is made to use the endoscope cover 307 for the fiber scope 301, to the video scope, it is impossible to apply covering to the switch portion. Accordingly, in order to mount the endoscope cover to the video scope, it has been required to prepare an endoscope cover for a video scope which is different from the endoscope cover 307 for the fiber scope 301.

In this manner, if a plurality of kinds or types of the endoscope cover 307 are required, there is a fear that erroneous mounting damages the endoscope cover 307, or incomplete mounting makes it impossible to be capable of preventing infection.

Figure 41:
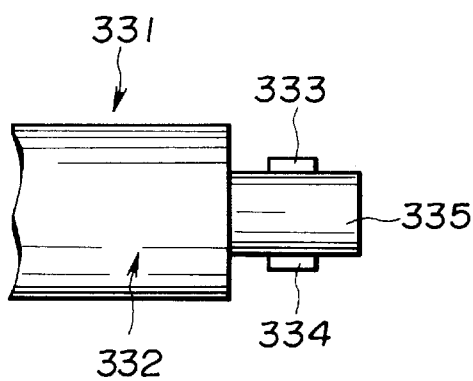

In view of the above, as shown in FIG. 41, form of a portion of an operating section 332 of a video scope 331 on the side of hand is formed into one substantially the same as the ocular portion 305 of the fiber scope 301, and a plurality of switches 333 and 334 are arranged at the portion, to form a switch portion 335. Specifically, the fiber scope 301 and the video scope 331 are made identical in outer appearance form of a portion, to each other, on which the endoscope cover 307 is mounted, that is, the inserting section 302, the operating section 303, the ocular portion 305 and the like. In this connection, it is needless to say, the fiber scope 301 and the video scope 331 are such that their respective observation optical system 312 and illuminating optical system 314 are provided at the same position, and the outer diameters of these inserting sections 302 are also formed substantially equal to each other.

In this manner, by the fact that the fiber scope 301 and the video scope 331 are coincident in outer appearance form to each other, the endoscope cover 307 can be used in common. Thus, it is possible to prevent such an accident that the sheath for the fiber scope and the sheath for the video scope are mounted in a mistake.

A fluid control unit will next be described with reference to FIGS. 42 to 45.

Figure 42:
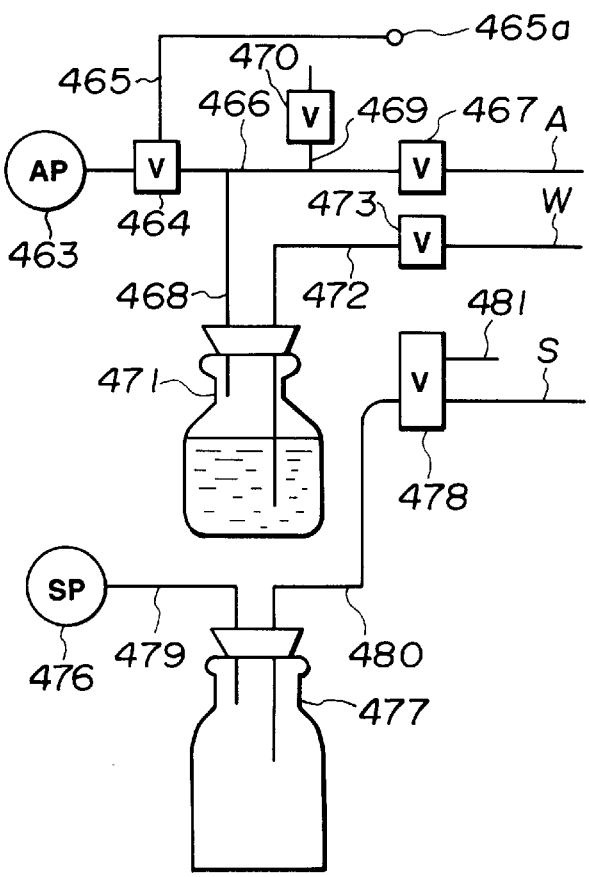
FIG. 42 is a line view relating to gas feeding, water feeding, suction and expansion.
Figure 43:
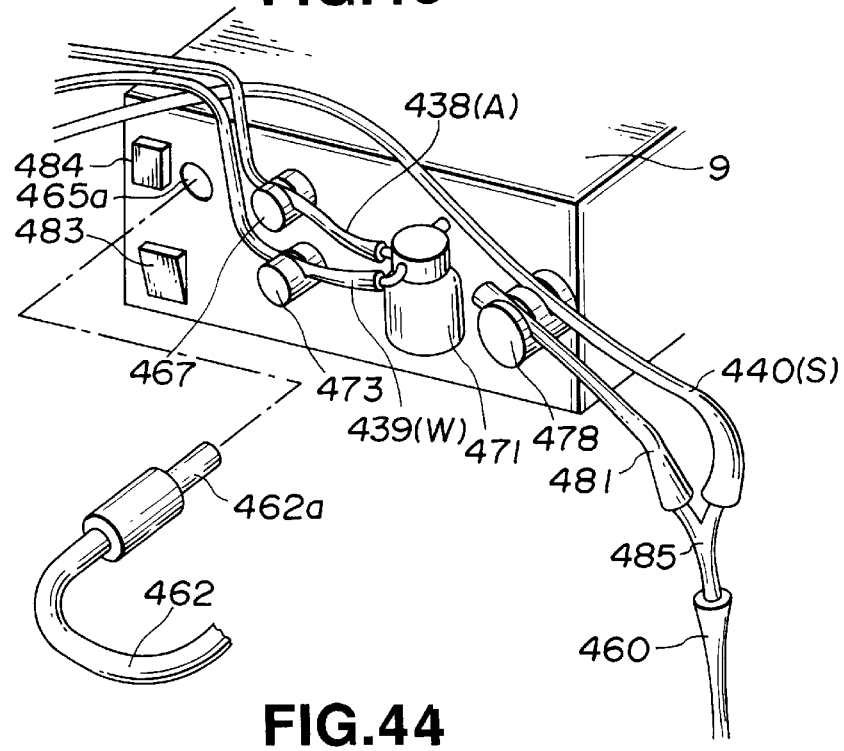
FIG. 43 is an outer appearance view on the side of a front elevation, showing an arrangement of a fluid control unit and a line.

FIG. 42 is a line view related to gas feeding, water feeding, suction and expansion or extension. As shown in FIG. 42, a gas feeding pump (AP) 463 that is a gas feeding source, and a first electromagnetic valve 464 which performs switching of gas feeding and extension are incorporated in a fluid control unit 9. The gas feeding pump 463 is in communication with the first electromagnetic valve 464 that is a port valve. The first electromagnetic valve 464 has one outlet thereof to which one end of an extension tube connecting line 465 is connected. The other end of the extension tube connecting line 465 is in communication with an opening 465*a* which is provided in the fluid control unit 9, as shown in FIG. 43. A connecting base 462*a* of an extension tube 462 is adapted to be detachably connected to the opening 465*a*. The extension tube 462 is adapted to be detachably connected to an extension tube port of the cover. The arrangement is such that extension of an endoscope inserting channel of the endoscope cover is performed through the extension tube 462.

Further, a first gas feeding line 466 is connected to the other outlet in the first electromagnetic valve 464. The first gas feeding line 466 is connected to a second electromagnetic valve 467 for controlling gas feeding. Gas feeding is performed through a gas feeding line $\underline{A}$ which is connected to the second electromagnetic valve 467.

A water feeding pressurizing line 468 branches from and is connected, on the way, to the first gas feeding line 466.

Moreover, a leak line 469 branches from and is connected to the first gas feeding line 466 at a location downstream of a branching point of the water feeding pressurizing line 468, for example. The leak line 469 communicates with the atmosphere through a third electromagnetic valve 470.

The water feeding pressurizing line 468 is in communication with a space above reserved liquid in a water feeding tank 471. A first water feeding line 472 is connected to the water feeding tank 471 under a condition that a suction port is dipped in the reserved liquid. A fourth electromagnetic valve 473 for controlling water feeding is connected to the first water feeding line 472. Water feeding is performed through a water feeding line $\underline{W}$ which is connected to the fourth electromagnetic valve 473.

Meanwhile, a suction system is arranged as follows:

A suction pump (SP) 476 shown in FIG. 42 is a suction source which is used in inspection, and is provided outside, for example, the fluid control unit 9. The suction pump 476 is in communication with a fifth electromagnetic valve 478 for controlling suction, through an internal space of a suction bin 477. The fifth electromagnetic valve 478 is a three (3)-port valve, and has two inlets and a single outlet.

The suction pump 476 is in communication with an internal space of the suction bin 477 through a first suction line 479. Moreover, a second suction line 480 which is in communication with the internal space of the suction bin 477 is connected to the outlet of the fifth electromagnetic valve 478.

The fifth electromagnetic valve 478 has one inlet thereof to which a suction leak pipe 481 in communication with the atmosphere is connected. Suction is performed through a suction line $\underline{S}$ which is connected to the other inlet. The fifth electromagnetic valve 478 is so arranged as to open and close the line and to switch communication between the outlet and the two inlets.

In connection with the above, the first to fifth electromagnetic valves are so arranged as to be controlled by a control section (not shown) which is provided on the fluid control unit 9.

The gas feeding, water feeding, suction and extension line systems as mentioned previously are specifically located at a front surface of the fluid control unit 9, and can be arranged and connected in configuration as shown, for example, in FIG. 43. In this connection, the reference numeral 483 in FIG. 43 denotes an electric power supply switch.

As shown in FIG. 43, a water feeding tank 471, and second, fourth and fifth electromagnetic valves 467, 473 and 478 are arranged at the front surface of the fluid control unit 9. Furthermore, a gas feeding pump 65, the first electromagnetic valve 464 and the third electromagnetic valve 470 are provided within the fluid control unit 9.

Further, a change-over switch 484 for changing over gas feeding function and gas feeding and water feeding function to the extension tube 462 is provided on the front surface of the fluid control unit 9. The change-over switch 484 is electrically connected to the control section. The arrangement is such that the control section is controlled by the second and fourth electromagnetic valves 467 and 473, whereby switching or changeover of the gas feeding and the water feeding is performed.

Here, the second, forth and fifth electromagnetic valves 467, 473 and 478 are of pinch valve type which crushes a tube to control the same. Accordingly, in the arrangement which uses the pinch valve type, the lines $\underline{A}$, $\underline{W}$, $\underline{S}$ illustrated in FIG. 42 form the following arrangement.

Specifically, the gas feeding line $\underline{A}$ is formed by the gas feeding pipe of the inserting-section cover portion and a gas feeding relay pipe 438 of a relay pipe in order from a portion adjacent to the forward end. Moreover, the gas feeding relay pipe 438 has a role including a part of the first gas feeding line 466, other than the gas feeding line A.

With the arrangement, gas which is fed from the gas feeding pump 463 passes through the gas feeding relay pipe 438 and the gas feeding pipe and is jetted from a gas feeding nozzle. Stoppage of gas feeding is performed such that the second electromagnetic valve 467 crushes the gas feeding relay pipe 438 to close the line.

Furthermore, the water feeding line W is formed by a gas feeding line of the inserting-section cover and water feeding relay pipe 439 of the relay pipe in order from the side of the forward end. The water feeding relay pipe 439 has a role including a part of the first water feeding line 472, other than the gas feeding line W.

With the arrangement described above, the gas fed from the gas feeding pump 463 passes through the gas feeding pressurizing line 468 to pressurize the reserved liquid within the water feeding tank 471. The liquid passing through the first gas feeding line 72, water, for example, passes through the water feeding relay pipe 439 and the water feeding pipe serving as the gas feeding line W and is jetted from the water feeding nozzle. Stoppage of the water feeding is performed such that the fourth electromagnetic valve 473 crushes the water feeding relay pipe 439, whereby the line is close.

Furthermore, in the arrangement illustrated in FIG. 43, since the fifth electromagnetic valve 478 is pinch valve type, the suction line S is so arranged as to use a Y-letter or Y-shaped branch pipe 485, differentiated from the arrangement illustrated in FIG. 42. Specifically, the suction line S is formed by the gas feeding line of the inserting-section cover portion and the gas feeding relay pipe 439 of the relay pipe in order from the side of the forward end. The fifth electromagnetic valve 478 is interposed between the gas feeding relay pipe 439 and a suction leak line 481, and the gas feeding relay pipe 439 and the suction leak line 481 are connected respectively to one end and the other end of the inlet of the Y-shaped branch pipe 485. Further, the Y-shaped branch pipe 485 has an outlet thereof to which the other end of the second section line 480 to one end of which the suction bin 477 is connected.

With the arrangement, suction pressure due to the suction pump 476 is transmitted to the opening through the suction relay pipe 440 and the suction pipe serving as the suction line S. Stoppage of suction is arranged such that the fifth electromagnetic valve 478 crushes the suction relay pipe 440, whereby the line is closed.

In connection with the above, if the fifth electromagnetic valve 478 is port type, the Y-shaped branch pipe 485 is unnecessary. As shown in FIG. 42, necessary or required pipes may be connected to various outlets and inlets of the ports. In this case, the gas feeding relay pipe 439 is connected to the side adjacent to the one inlet of the port.

Various operations of gas feeding, water feeding, suction and extension will be described next.

Control of the gas feeding, water feeding and suction are performed as follows. The gas feeding and water feeding will first be described. Upon waiting, the third electromagnetic valve 470 opens, and the second and fourth electromagnetic valves 467 and 73 are closed under a condition that the outlet of the first electromagnetic valve 464 opens toward the first gas feeding line 466. That is, gas feeding and water feeding are not performed.

Next, gas feeding is arranged such that, when the gas feeding and water feeding switch is turned ON under a condition that the change-over switch, for example, is turned OFF, the third electromagnetic valve 470 is closed, and the second electromagnetic valve 467 opens so that gas feeding is performed.

Meanwhile, water feeding is arranged such that, when the change-over switch, for example, is turned ON, the gas feeding and water feeding switch is turned ON, whereby the third electromagnetic valve 470 is closed, and the fourth electromagnetic valve 473 opens so that water feeding is performed. In this connection, water feeding and gas feeding may be performed simultaneously.

Suction is performed as follows.

While waiting, a suction control switch, for example, is turned OFF, the side of the suction leak line 481 opens, and the side of the third suction line 480 is closed. The suction leak pipe 481 is brought to a communicating condition by the fifth electromagnetic valve 478. Suction is brought to a stopped condition, and a condition is brought to a condition under which suction from the suction line is not performed.

Meanwhile, suction is performed by the fact that, when the suction control switch, for example, is turned ON, operation of the fifth electromagnetic valve 478 becomes reverse to the above-described operation.

Since the present embodiment is so arranged as to share or use in common the gas feeding pump of the fluid control unit 9 for extension of the inserting-section cover portion, without additional providing of an extension pump, an expander can be made unnecessary or can be dispensed with. In this manner, in the present embodiment, the functions including the extension function of the channel and the function of gas feeding and water feeding are retained or held, while constitutional waste is omitted, and an attempt can be made to reduce, in size, or miniaturize the apparatus. In this connection, the present embodiment is effective also for an arrangement in which only one of gas feeding and water feeding is performed.

The light source unit will be described with reference to FIGS. 44 and 45.

The present embodiment shows an arrangement in which a gas feeding pump which is provided within the light source unit is used as an expander. The other arrangement and function are similar to those of the embodiment illustrated in FIGS. 42 and 43. The same reference numerals are applied to the same or identical elements, and the description thereof will be omitted.

Figure 44:
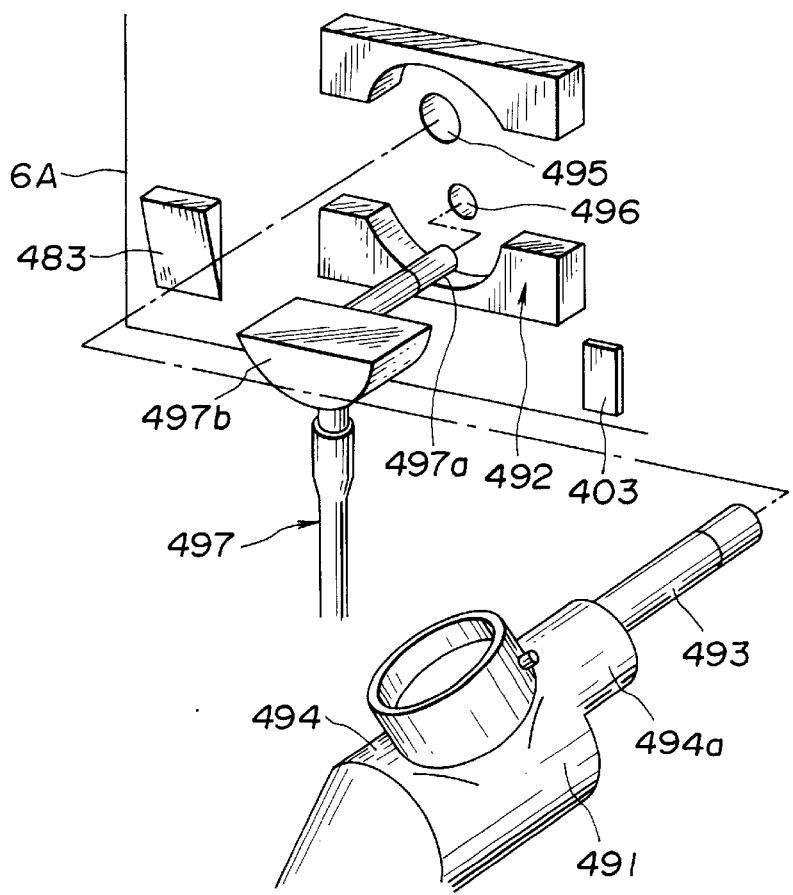
FIG. 44 is an enlarged view showing a partial front surface of the light source unit.
Figure 45:
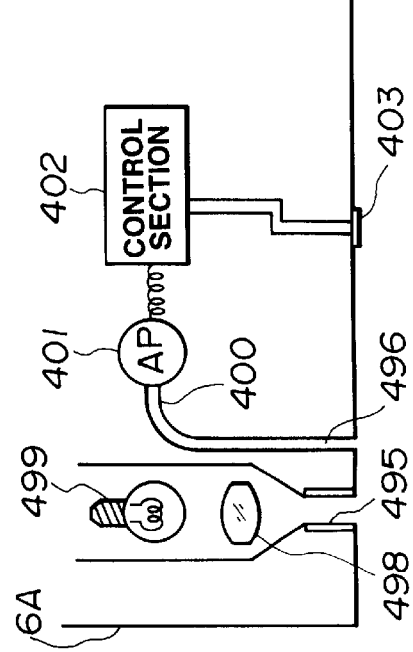
FIG. 45 is a view showing a schematic arrangement of the inside of the light source unit.
Figure 47:
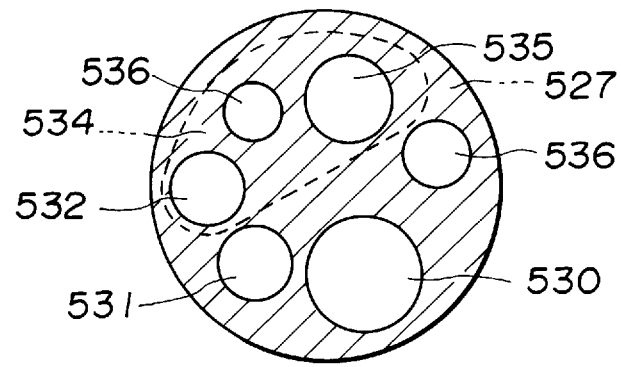
FIG. 47 is a cross-sectional view showing a forward end of the endoscope cover illustrated in FIG. 46.

FIG. 44 shows, in enlargement, the arrangement of a connector receptor portion 492 of a light source unit 6A. An illuminating base 493 in which an illuminating light guide fiber (not shown) is mounted projects from a receptor body 494 at a forward end of a connector 491. The receptor body 494 of the connector 491 is cylindrical, and a cut-off portion 494a is formed on the side of a forward end of the receptor body 494.

The illuminating base 493 of the connector 491 is adapted to be detachably connected to a light guiding bore 495 which is provided in the connector receptor portion 492. An extension tube connecting port 496 is provided below the light guiding bore 495 so that a connecting base 497a of an extension tube 497 is detachably connected. An engaging element 497b which is engaged with the cut-out portion 494a is interposed in the extension tube 497 on the way of a line. The engaging element 497b of the extension tube 498 is engaged, together with the connector 491, with the connector receptor portion 492 so as to be held. A condensing lens 497 and a light source lamp 499 as shown in FIG. 45 are arranged in rear of the light guiding bore 495. The illuminating light from the light source lamp 499 is supplied to the light guide fiber under a condition that the connector 491 is mounted on the light guiding bore 495.

Further, a gas feeding pump (AP) 401 serving as a gas feeding source is arranged in rear of a line 400 which is in communication with a connecting port 496. The gas feeding pump 401 is a gas feeding source for gas feeding, water feeding and extension, and is adapted to be controlled in ON/OFF by a control section 402. A switch 403 for controlling operation of the gas feeding pump 401 is electrically connected to the control section 402.

In the arrangement described above, it is possible to use the gas feeding pump 401 which is provided on a light source unit 6A, as a gas feeding source of gas feeding, water feeding and extension, in place of the gas feeding pump 463 which is provided on the fluid control unit 9. In this connection, in this arrangement, the gas feeding pump 401 and the inlet of the first electromagnetic valve 464 are in communication with each other and are connected to each other.

Moreover, apart from the above-described arrangement, operation in a case where the light source unit 6A is used as an expander will be described. The connecting base 497a of the extension tube 497 is first connected to the connecting port 496. The other end of the extension tube 497 is next connected to the extension tube port. When a switch 403 is turned ON, gas feeding is performed into the extension tube 497. Thus, mounting of the covering endoscope inserting section on the inserting-section cover portion can be easily performed.

In the present embodiment, an existing light source unit is used whereby a gas feeding source for extension function is not required to be provided on the fluid control unit.

Further, in a case where the gas feeding pump 401 is used as a gas feeding source for gas feeding and water feeding, one end of the gas feeding pump 401 is in communication with and is connected to the inlet or entrance of the electromagnetic valve 464, and the other end (not shown) is connected to the connecting port 496. With the arrangement described above, since the line is selectively connected, and an attempt is made for commonization of the gas feeding source, an extension line connecting tube 65 is not connected to the outlet of the first electromagnetic valve 464.

In connection with the above, the present embodiment is applicable to an endoscope having no gas feeding and water feeding function, for example, an endoscope for bronchus. In this example, the fluid control unit 9 is made unnecessary or is dispensed with, but the light source unit 7 is necessary or is required. For this reason, an arrangement in which a gas feeding pump 401 is incorporated in the existing light source unit 6A is used with respect to the endoscope for bronchus so that mounting and demounting of the inserting-section cover portion can be performed. Here, the arrangement described above is different only in that it has no gas feeding and water feeding function, and is similar to that described previously in a detaching mechanism for the inserting cover portion and operation and advantages thereof.

In connection with the above, the present invention is not limited to an electronic type endoscope, but is also effective for an optical fiber endoscope, and an ultrasonic endoscope, for example.

Another embodiment of the invention will be described with reference to FIG. 46 to FIG. 49.

Figure 46:
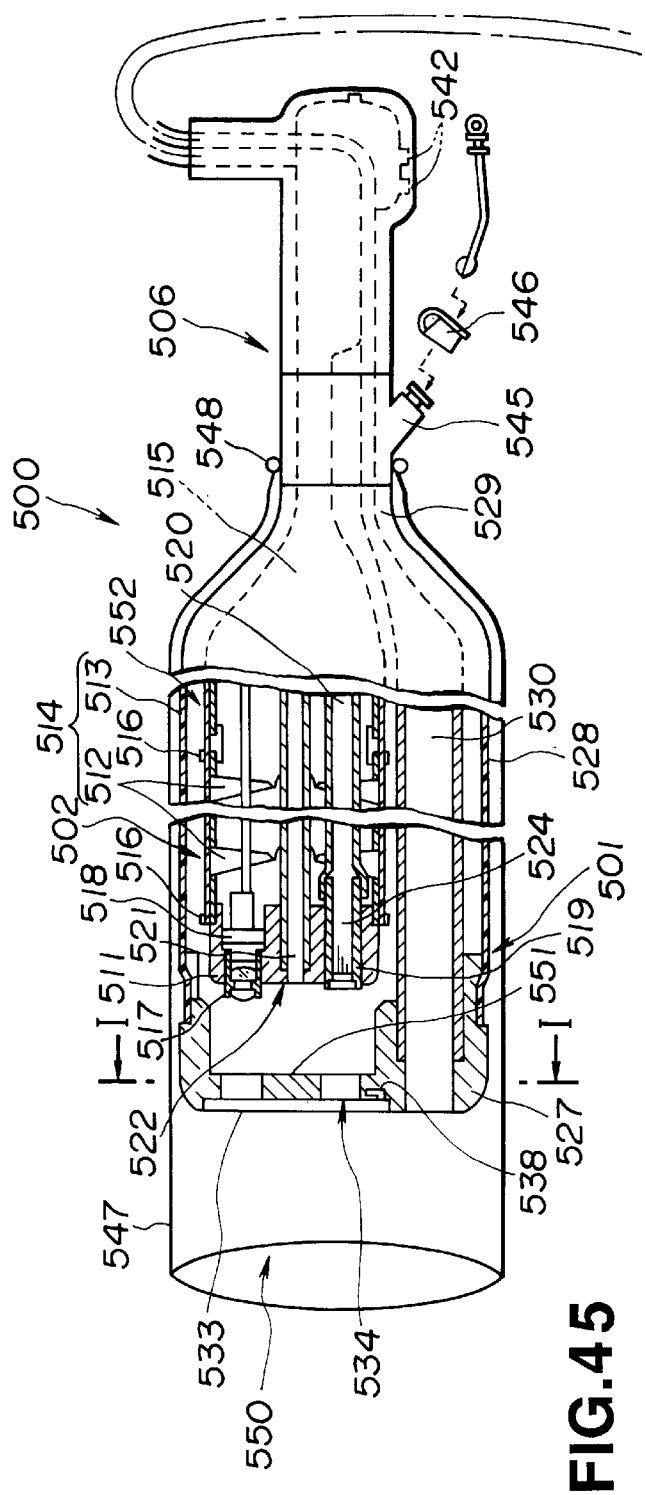
FIG. 46 is a cross-sectional view showing a mounting condition of the covering endoscope on the endoscope cover.

As shown in FIG. 46, a cover-type endoscope system 500 comprises an endoscope cover 501, a covering endoscope 502, a light source unit 503, a video processor 504, and a fluid control unit 505.

The covering endoscope 502 comprises a forward-end rigid portion 511 which is formed by black plastics and whose cross-sectional form is substantially D-shaped, a plurality of joint pieces 512 connected to the forward-end rigid portion 511, whose cross-sectional form is substantially D-shaped, for converting a field-of-view direction of the endoscope, a curvature portion 514 having elastomers tube 513 which is cylindrical under a natural condition, for covering the joint piece 512, and an inserting section 515 connected to the curvature portion 514, of three-layer structure including a helical metallic plate, a metallic net pipe and a resinous pipe and having a circular cross-section.

The elastomers pipe 513 has both ends 516 thereof which are arranged such that threads or yarns are wound and are fixedly mounted, adhesives are applied onto the threads, to form a bulge portion which projects more than the outer form of the elastomers pipe 513 (inserting section). Both ends 516 serve as guide surfaces at the time of insertion and withdrawal into and from an endoscope inserting passage which is provided in the endoscope cover 501.

Formed in the forward-end rigid portion 511 are a through bore within which an objective frame 517 which accommodates therein an observation optical system 518 such as an objective lens, and a CCD is arranged, a through bore in which an illuminating frame 519 which accommodates therein an end of an illuminating optical system 524 such as an illuminating lens, and a light guide fiber, is arranged, a bore 521 in which an inflator line 520 to be described subsequently is arranged, and the like.

The objective frame 517 and the illuminating frame 519 are so provided as to project more than an end surface 522 of the forward-end rigid portion 511. At this time, this is because it is easier in working or processing that the objective frame 517 and the illuminating frame 519 are arranged at and project a through bore formed in the forward-end rigid portion 511 than an arrangement that a projection is formed on the forward-end rigid portion 511, and the observation optical system or the illuminating optical system is arranged at the projection, and a position and an amount of projection of the objective frame 517 or the illuminating frame 519 from the forward end surface 522 can be regulated or adjusted as the occasion demands.

Further, the amount of projection between the objective frame 517 and the illuminating frame 519 is the same or, alternatively the objective frame 517 projects slightly more than the illuminating frame 519. Specifically, when it is assumed that a distance between the end surface of the objective frame 517 and the forward end surface 522 is 0.3 mm, a distance between an end surface of the illuminating frame 519 and the forward end surface 522 is 0.1 mm. That is, specifically, a difference in the amount of projection is contended is set within a range of 0 mm~0.5 mm.

Forms of an arranged position and a mechanical coupling portion of an electric-signal contact of a connecting portion of the connecting cord 523 which is connected to the video processor 504 connected to the connector 507 are so formed as to be the same as the forms of an arranged position and a mechanical coupling portion of an electric-signal contact of a reusable type endoscope. For this reason, the arrangement is such that any of the cover type endoscope and the reusable type endoscope can freely be used without replacement or exchange of a connecting cord 523 or the video processor 504.

An outer diameter, a length and a form of the illuminating-light receiving portion and a form of an air receiving portion of a light-source connector portion 526 which is connected to the light source unit 503 are so formed as to be the same as an outer form, a length and a form of an illuminating-light receiving portion and a form of an air receiving portion which are provided on the connector of the reusable type endoscope. For this reason, any of the reusable type endoscope and the cover type endoscope can freely be used without replacement of the light source unit 503. In this connection, it is possible to integrally provide the light-source connector portion 526 on the connector 507.

Figure 48:
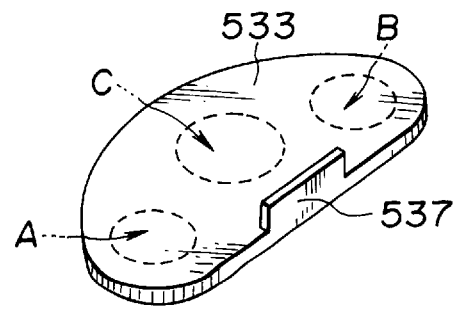
FIG. 48 is a perspective view showing a lens cover which is arranged in FIG. 46.

The endoscope cover 501 comprises a forward-end constitutional portion 527 formed by, for example, a black resinous element, and an envelope 528 and a port portion 529 made of a soft tube material such as urethane or vinyl chloride whose thickness is 0.1 mm to 0.5 mm. The forward-end constitutional portion 527 is formed therein with a suction and treatment line 530, an opening 531 of a gas feeding line (FIG. 47), and an opening 532 (FIG. 47) of a water feeding line. A plastic transparent body 533 of substantially semicircle illustrated in FIG. 48 is fixedly mounted on a stepped bore 534 which is provided with an objective bore 535 into which the objective frame 517 is inserted, and an illuminating bore 536 into which two (2) illuminating frames 519 are inserted.

The plastic transparent body 533 is a plastic compact such as, for example, a polycarbonate. Gate portions 537 formed upon forming or molding are provided respectively out of an optical region including an illuminating-light outgoing region (broken regions A and B ) and an observation-light incident region (broken region C), as shown in FIG. 48. Accordingly, since it is unnecessary to polish or hand-finish the gate portion 537, polishing which tends to optically hinder or impede can be omitted.

Moreover, even if the gate portion 537 projects, a recess 538 is provided in the forward-end constitutional portion 527 such that the plastic transparent body 533 is reliably fixed to the forward-end constitutional portion 527.

Here, a method of mounting the covering endoscope 502 on the endoscope cover 501 and a mechanism for the mounting will briefly be described with reference to FIG. 46.

The covering endoscope 502 is formed therein with the gas feeding line 520. The gas feeding line 520 has one end 521 thereof which opens and another end which is in communication with a fluid control unit port 539 in a connector 507. At an opening of the one end 521, air sent out from a pump 540 which is provided on the light source unit 503 is once sent into a fluid control unit through the light-source connector 526 and, thereafter, is sent out through an electromagnetic valve of the fluid control unit 505 and a connecting tube 541. An inflator switch which is provided in the fluid control unit 505 is actuated or operated whereby the electromagnetic valve opens so that the air is released. A space portion of an internal space within the inserting-section cover portion 528 except the suction line 530, the gas feeding line 531 and the water feeding line 532 form an endoscope inserting passage 552. If the forward-end rigid portion 511 is inserted from the port 529 while the air is released from the opening 521, the endoscope inserting passage 552 is expanded by air pressure so that a clearance between the covering endoscope 502 and the endoscope inserting passage 552 increases. Thus, it is possible to insert the covering endoscope 502 into the endoscope inserting passage 552 with less frictional resistance.

In connection with the above, since the gas is fed from the opening 521 which is provided in the forward-end rigid portion 511 of the covering endoscope 502, the fed gas (air) passes through a clearance between the covering endoscope 502 and the endoscope inserting passage 552, and is released to the outside. Thus, since the gap is secured over the entire length of a mounting region between the covering endoscope 502 and the endoscope inserting passage 552, the frictional resistance can be reduced to insert the covering endoscope 502 into the endoscope cover 501, less than the arrangement that air is fed from the vicinity of the envelope 528, as in U.S. Pat. No. 4,646,722.

Further, the covering endoscope 502 is gradually inserted into the endoscope inserting passage 552 while the air continues to be fed. When the illuminating frame 519 and the forward-end constitutional portion 527 approach each other (a condition illustrated, for example), the inflator switch is turned off, and the gas feeding stops. The illuminating frame 519 is fixedly mounted within the forward-end constitutional portion 527. If the gas is fed to the end or last as is in the conventional arrangement, the pressure of the air between the illuminating frame 519 and the forward-end constitutional portion 527 increases or rises. If an attempt is made such that the illuminating frame 519 is mounted on the forward-end constitutional portion 527, the resistance due to the compressed air is high so that mounting is difficult. However, according to the arrangement of the invention, since gas feeding is suspended or discounted at the time the space portion defined by the illuminating frame 519, and the forward-end constitutional portion 527 and the observation optical system 518 decreases, it is possible to easily mount the illuminating frame 519. In this connection, in a case where the covering endoscope 502 is removed or drawn out from the endoscope cover 501, the inflator switch of the fluid control unit 505 is operated or activated so that gas is fed from the opening 521 to draw out the covering endoscope 502.

As described previously, the fact that projections larger than the outer form of the inserting section are formed respectively at both ends of the inserting section (elastomer pipe) of the covering endoscope, the entire or whole periphery of the elastomer pipe does not directly slide with respect to the inner peripheral surface of the endoscope cover. Accordingly, repeated replacement or exchange does not wear or abrade the elastomer pipe. In this connection, similar advantages can be produced even if a thermally shrinking tube or a plastic tube is arranged in place of the fact that adhesives are applied to both ends of the elastomer pipe to form projections.

By the way, when the covering endoscope 502 is polluted or contaminated before inspection is performed or before the endoscope cover 501 is covered, it is necessary to clean and disinfect the endoscope for safety. At this time, a portion to which the video processor connecting code 523 of the connector 507 is connected and the fluid control unit port 539 are covered by an integrally or separately formed waterproof cap (not shown) and are cleaned and disinfected. Thus, it is possible to prevent corrosion of a contact which is connected to a contact of the video processor connecting code 523, and it is possible to minimize invasion of water into the gas feeding line 520.

In this manner, the remaining water within the gas feeding line after cleaning and disinfection is reduced whereby gas feeding is performed by the fluid control unit 505 so that it is possible to perform draining in a shorter period of time. Moreover, when the covering endoscope 502 is inserted into the endoscope cover 501, there is no case where water remains within the inside and is adhered to an objective surface so that a field-of-view is hurt or injured. Of course, if a waterproof cap is mounted on the opening 521 to perform cleaning and disinfection, it is possible to completely prevent water from invading.

Meanwhile, the fluid control unit 505 has functions of suction from the suction line 530, gas feeding into the gas feeding line 531 and water feeding to the water feeding line 532, in addition to the inflator function. An electromagnetic valve within the fluid control unit 505 is controlled by a signal from the switch 542 which is provided on the operating section 506, so that suction, gas feeding and water feeding are performed respectively through suction, gas feeding and water feeding tubes 544, 544 and 544. The gas feeding pump 540 is used as a gas feeding source, while a suction pump 543 is used as a suction source.

In connection with the above, since the form of an end of a tube 544 connected to the fluid control unit 505 is the same as the form of the end of the suction, gas feeding and water feeding tube of the reusable type endoscope, any of the cover type endoscope and the reusable type endoscope can be mounted without replacement or exchange of the fluid control unit 505.

The port 529 is provided with a forceps opening 545 which is in communication with the suction line 530. A forceps plug 546 is adapted to be mounted on the forceps opening 545. A form of a mounting portion thereof is the same as a form of a forceps-plug mounting portion of the reusable type endoscope. Accordingly, the forceps plug 546 can be used to any of the reusable type endoscope and the cover type endoscope.

In connection with the above, a size or dimension of an inner diameter of the suction line 530 is the same as the size of an inner diameter of the suction and treatment line of the reusable type endoscope, or is slightly larger than the same. Accordingly, even in a case where the reusable type endoscope and the cover type endoscope are replaced from each other and are used, it is possible to use the treatment equipment 546 of the same type.

By the way, a pollution preventing protective pipe 547 is covered on the endoscope cover 501 until inspection starts. The protective pipe 547 has one end thereof which is provided with a resilient or flexible ring 548. The protective pipe 547 is adapted to be fixed to the neighborhood of the forceps opening 545 by a flexible force of the flexible ring 548. The protective pipe 547 has a length sufficient to cover the entire endoscope cover. A second opening 550 is formed in the other end of the protective pipe 547.

Figure 49:
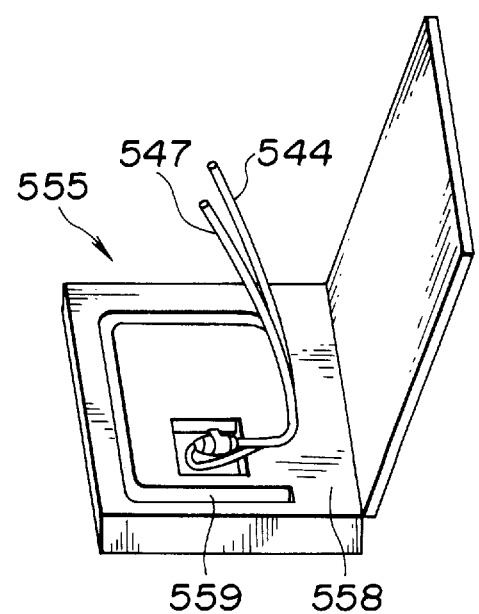
FIG. 49 is a perspective view showing an example of an accommodating or receiving condition onto a receiving tray.

As shown in FIG. 49, when the endoscope cover 501 in which the protective pipe 547 is mounted in a groove 559 in a flexible element 558 is received in a receiving tray 555, air between the protective pipe 547 and the endoscope cover 501 escapes from the second opening 550. Accordingly, an air reservoir is not formed at a receiving portion so that the endoscope cover 501 can easily be received in the groove 559.

In connection with the above, under a condition when the covering endoscope 502 is mounted on the endoscope cover 501, the forward end surface 522 comes into collision with or is abutted against the inward surface 551 of the forward-end constitutional portion 527. At this time, the end surfaces of the respective objective frame 517 and illumination frame 519 are so arranged as not to be in contact with the plastic transparent body 533. For this reason, even if the forward-end rigid portion 511 is pressed or forced into the side of the forward end in an attempt to secure that the covering endoscope 502 is fixed to the endoscope cover 501, a stress is not directly applied to the plastic transparent body 533. Accordingly, it is possible to prevent a junction or joining portion between the forward-end constitutional portion 527 and the plastic transparent body 533 is destroyed or broken, and bacteria and filth or dirt enter from the gap so that the covering endoscope is contaminated.

By the way, the objective frame 517 and the illuminating frame 519 project more than the forward-end surface 522. Accordingly, when the covering endoscope 502 is mounted on the endoscope cover 501, the objective frame 517 gets into the objective bore 535, and the illuminating frame 519 gets into the illuminating bore 536. Since the forward-end constitutional portion 527 is formed by a light shielding element, light is prevented from coming into the objective frame 517 from the illuminating frame 519.

In connection with the above, since it is set that the objective frame 517 is larger or the same in amount of projection than or as the illuminating frame 519, a distance from the objective bore 535 to the objective lens surface is larger than or the same as a distance from the objective bore 535 to the illuminating lens surface. At this time, a distance between the objective bore 535 and the objective lens is larger in affection or influence with respect to abnormality of a field-of-view such as objective flare, ghost and the like than a distance between the objective bore 535 and the illuminating lens. Accordingly, since, in the present system, there is no fear that the illuminating lens interferes with the objective bore 535, it is possible to easily adjust or regulate positions of the objective bore 535 and the objective lens.

It is claimed:

1. An endoscope system comprising:

at least one reusable type endoscope provided therein with an illuminating optical system, an observation and a flow passage system, wherein cleaning and disinfection is applied to said reusable type endoscope provided with an elongated insertion tube, an operation part connected to the proximal end of the insertion tube, a connector of said reusable type endoscope having at least one connection part connected to the illumination optical system and the flow passage system, and an elongated and flexible cord connecting said operation part and said connector of said reusable type endoscope so that said reusable type endoscope is used;

at least one cover type endoscope provided therein with an illuminating, optical system and an observation system, said cover type endoscope having an elongated insertion tube, an operation part connected to the proximal end of the insertion tube, a connector of said cover type endoscope having a connection part connected to the illuminating optical system, and an elongated and flexible cord connecting said operation part and said connector of said cover type endoscope, said cover type endoscope including an endoscope cover having a flow passage system mounted in said cover, said endoscope cover being discarded and replaced whenever said cover type endoscope is reused; and a light source, which is peripheral equipment adaptable for use during endoscope inspection, for providing illuminating light, said light source unit including connecting means for selectively connecting said connector of said reusable type endoscope and said connector of said cover type endoscope to said light source unit; and wherein an observation range and a displayed image which are produced by said reusable type endoscope and an observation range and a displayed image which are produced by said cover type endoscope are substantially equal in size;

wherein at least one of said endoscopes is a reusable type electronic endoscope and another of said endoscopes is a cover type electronic endoscope, and wherein, in order that the observation range which is produced by said reusable electronic endoscope and the observation range which is produced by said cover type electronic endoscope are similar to each other, the angle of view of said reusable type electronic endoscope and the angle of view of the cover type electronic endoscope are equal to each other;

wherein, in order that the angle of view of said reusable type electronic endoscope and the angle of view of the cover type electronic endoscope are equal to each other, a light beam height of an incident first plane of the observation optical system of the cover type electronic endoscope is less than a light beam height of an incident first plane of the observation optical system of the reusable type electronic endoscope; and wherein, in order that the light beam height of the incident first plane of the observation optical system of the cover type electronic endoscope is less than the light beam height of the incident first plane of the observation optical system of said reusable type electronic endoscope, an incident pupil diameter of the observation optical system of the covering electronic endoscope of the cover type electronic endoscope is less than an incident pupil diameter of the observation optical system of the reusable type electronic endoscope.

2. An endoscope system according to claim 1, wherein at least one of said endoscopes is a reusable type fiber scope and another of said endoscopes is a cover type fiber scope, wherein mask means for making the observation region of a reusable type fiber scope substantially equal in size to the observation region of a cover type fiber scope is arranged between said observation optical system and an ocular portion of each said endoscope.

3. An endoscope system according to claim 1, wherein at least one of said endoscopes is a reusable type electronic endoscope and another of said endoscopes is a cover type electronic endoscope, and wherein, in order that the displayed. image region produced by said reusable type electronic endoscope is substantially equal in size to the displayed image region. produced by said cover type electronic endoscope, said endoscope. system further comprises a mask processing means for. electrically performing mask processing with respect to an electrical signal which is photoelectrically converted by image pickup means.

4. An endoscope system comprising:

at least one reusable type endoscope provided therein with an illuminating optical system, and observation system and a flow passage system, wherein cleaning and disinfection is applied to said reusable type endoscope provided with an elongated insertion tube, an operation part connected to the proximal end of the insertion tube, a connector of said reusable type endoscope having at least one connection part connected to the illuminating optical system and the flow passage system, and an elongated and flexible cord connecting said operation part and said connector of said reusable type endoscope so that said reusable type endoscope is used;

at least one cover type endoscope provided therein with an illuminating optical system and an observation system, said cover type endoscope having an elongated insertion tube, an operation part connected to the proximal end of the insertion tube, a connector of said cover type endoscope having a connection part connected to the illuminating optical system, and an elongated and flexible cord connecting said operation part and said connector of said cover type endoscope, said cover type endoscope including an endoscope cover having a flow passage system mounted in said cover, said endoscope cover being discarded and replaced whenever said cover type endoscope is reused; and a light source unit, which is peripheral equipment adaptable for use during endoscope inspection for providing illuminating light, said light source unit including connecting means for selectively connecting said connector of said reusable type endoscope and said connector of said cover type endoscope to said light source unit, wherein the cover type endoscope has an inserting section which is inserted into said endoscope cover, said inserting section including a flexible cover having both ends thereof provided with bulge portions which project from an outer form of said inserting section, said bulge portions serving as a guide surface upon insertion into said endoscope cover.

5. An endoscope system according to claim 4, wherein said bulge portions are formed by hardened adhesives.

* * * * *